United States Patent
Gareau et al.

(10) Patent No.: US 10,182,757 B2
(45) Date of Patent: Jan. 22, 2019

(54) SYSTEM AND METHOD FOR OPTICAL DETECTION OF SKIN DISEASE

(71) Applicant: The Rockefeller University, New York, NY (US)

(72) Inventors: Daniel Gareau, New York, NY (US); Justin Martin, New York, NY (US)

(73) Assignee: THE ROCKEFELLER UNIVERSITY, New York, NY (US)

( * ) Notice: Subject to any disclaimer, the term of this patent is extended or adjusted under 35 U.S.C. 154(b) by 103 days.

(21) Appl. No.: 14/051,053

(22) Filed: Oct. 10, 2013

(65) Prior Publication Data

US 2015/0025343 A1 Jan. 22, 2015

Related U.S. Application Data

(60) Provisional application No. 61/857,143, filed on Jul. 22, 2013.

(51) Int. Cl.
| | |
|---|---|
| A61B 5/00 | (2006.01) |
| A61B 5/103 | (2006.01) |
| A61B 5/1455 | (2006.01) |
| A61B 5/145 | (2006.01) |

(52) U.S. Cl.
CPC ............ *A61B 5/444* (2013.01); *A61B 5/0075* (2013.01); *A61B 5/14546* (2013.01); *A61B 5/14551* (2013.01); *A61B 5/14552* (2013.01); *A61B 5/443* (2013.01); *A61B 5/6898* (2013.01); *A61B 2560/0431* (2013.01); *A61B 2576/00* (2013.01)

(58) Field of Classification Search
None
See application file for complete search history.

(56) References Cited

U.S. PATENT DOCUMENTS

| | | | |
|---|---|---|---|
| 5,016,173 A | | 4/1991 | Kenet et al. |
| 5,706,821 A | * | 1/1998 | Matcher ............ A61B 5/14553 250/330 |
| 5,944,598 A | * | 8/1999 | Tong ...................... A22B 5/007 382/100 |
| 6,208,749 B1 | | 3/2001 | Gutkowicz-Krusin et al. |
| 7,006,223 B2 | | 2/2006 | Mullani |
| 7,027,153 B2 | | 4/2006 | Mullani |
| 7,167,243 B2 | | 1/2007 | Mullani |

(Continued)

FOREIGN PATENT DOCUMENTS

| | | |
|---|---|---|
| CN | 101686819 | 3/2010 |
| GB | 2502672 | 12/2013 |

(Continued)

OTHER PUBLICATIONS

International Search Report issued for International Application No. PCT/US14/47636, dated Feb. 13, 2015.

(Continued)

*Primary Examiner* — Patricia J Park
(74) *Attorney, Agent, or Firm* — Pearl Cohen Zedek Latzer Baratz LLP

(57) ABSTRACT

An optical system for the detection of skin disease, such as melanoma, acquires images of a lesion on a subject's skin at different wavelengths and utilizes a sweeping arm rotating about the lesion in a clock-like sweep to produce diagnostically relevant metrics and classifiers from the image data so as to enhance detection of the skin disease.

29 Claims, 12 Drawing Sheets

(56) References Cited

U.S. PATENT DOCUMENTS

| | | | |
|---|---|---|---|
| 7,167,244 | B2 | 1/2007 | Mullani |
| 7,603,031 | B1 | 10/2009 | Vlaud |
| 7,894,651 | B2 | 2/2011 | Gutkowicz-Krusin et al. |
| 8,218,862 | B2 | 7/2012 | Demirti |
| 8,498,460 | B2 | 7/2013 | Patwardhan |
| 8,971,609 | B2 | 3/2015 | Gareau et al. |
| 2003/0078482 | A1 | 4/2003 | Kenan |
| 2004/0267102 | A1* | 12/2004 | Skladnev ............... A61B 5/442 600/315 |
| 2005/0228264 | A1* | 10/2005 | Grichnik ............. A61B 5/0059 600/411 |
| 2008/0123106 | A1 | 5/2008 | Zeng et al. |
| 2008/0132794 | A1 | 6/2008 | Alfano et al. |
| 2008/0214907 | A1 | 9/2008 | Gutkowicz-Krusin et al. |
| 2008/0275315 | A1 | 11/2008 | Oka et al. |
| 2009/0016491 | A1* | 1/2009 | Li .......................... A61B 6/032 378/98.5 |
| 2009/0220415 | A1 | 9/2009 | Shachaf et al. |
| 2009/0279760 | A1* | 11/2009 | Bergman ............... G06T 7/0012 382/128 |
| 2010/0185064 | A1* | 7/2010 | Bandic ................. A61B 5/0059 600/306 |
| 2010/0255795 | A1 | 10/2010 | Rubinsky et al. |
| 2010/0271470 | A1 | 10/2010 | Stephan et al. |
| 2010/0302358 | A1 | 12/2010 | Chen |
| 2011/0013006 | A1 | 1/2011 | Uzenbajakava et al. |
| 2012/0041284 | A1 | 2/2012 | Krishnan et al. |
| 2012/0041285 | A1 | 2/2012 | Krishnan et al. |
| 2012/0170828 | A1 | 7/2012 | Gareau et al. |
| 2012/0172685 | A1 | 7/2012 | Gilbert |
| 2012/0259229 | A1 | 10/2012 | Wang |
| 2012/0320340 | A1 | 12/2012 | Coleman, III |
| 2013/0014868 | A1 | 1/2013 | Ishida |
| 2013/0053701 | A1 | 2/2013 | Wiest et al. |
| 2013/0108981 | A1 | 5/2013 | Duret |
| 2014/0036054 | A1 | 2/2014 | Zouridakis |
| 2014/0213909 | A1 | 7/2014 | Mestha |
| 2015/0025343 | A1 | 1/2015 | Gareau et al. |
| 2015/0082498 | A1 | 3/2015 | Meyer |

FOREIGN PATENT DOCUMENTS

| | | |
|---|---|---|
| JP | 2005192944 | 5/2005 |
| WO | WO 90/13091 | 11/1990 |
| WO | WO 2011/087807 | 7/2011 |
| WO | WO2012/162596 | 11/2012 |
| WO | WO2015/013288 | 1/2015 |

OTHER PUBLICATIONS

"Melanoma." Skin Cancer. Skin Cancer Foundation, n. d. Web. Jul. 29, 2013. <http://www.skincancer.org/skin-cancer-information/melanoma>.
Busam, Klaus J., Ashfaq A. Marghoob, and Allan Halpern. "Melanoma Diagnosis by Confocal Microscopy: Promise and Pitfalls." Journal of Investigative Dermatology. 125.3 (2005): n. page. Print.
Gareau, Daniel S., Glenn Merlino, Christopher Corless, Molly Kulesz-Martin, and Steven L. Jacques. "Noninvasive Imaging of Melanoma with Reflectance Mode Confocal Scanning Laser Microscopy in a Murine Model." Journal of Investigative Dermatology. (2007): n. page. Print.
Gareau, Dan. "Automated identification of epidermal keratinocytes in reflectance confocal microscopy."Journal of Biomedical Optics. 16.3 (2011): n. page. Print.
Gareau, Dan, Ricky Hennessy, Eric Wan, Giovanni Pellacani, and Steven L. Jacques. "Automated detection of malignant features in confocal microscopy on superficial spreading melanoma versus nevi." Journal of Biomedical Optics. 15.6 (2010): n. page. Print.
Nehal, Kishwer S., Dan Gareau, and Milind Rajadhyaksha. "Skin Imaging With Reflectance Confocal Microscopy." Seminars in Cutaneous Medicine and Surgery. 27. (2008): 37-43. Print.
Argenziano, G. et al., Dermoscopy improves accuracy of primary care physicians to triage lesions suggestive of skin cancer. J Clin Oncol, 2006. 24(12): p. 1877-82.
Artificial intelligence—how far can it go in dermatology? Modernizing Medicine Jul. 12, 2016; Available from: https://www.modmed.com/artificial-intelligence-how-far-can-it-go-in-dermatology/.
Breiman, L., Random Forests. Machine Learning, 45, 2001 Kluwer Academic Publishers. 5-32.
Cortes, C. and V. Vapnik, Support-vector networks. Machine Learning, 1995. 20(3): p. 273-297.
Doyle-Lindrud, S., Watson will see you now: a supercomputer to help clinicians make informed treatment decisions. Clin J Oncol Nurs, 2015. 19(1): p. 31-2.
Drugge, R.J., et al., Melanoma screening with serial whole body photographic change detection using Melanoscan technology. Dermatol Online J, 2009. 15(6): p. 1
Elder, D.E., Dysplastic naevi: an update. Histopathology, 2010. 56(1): p. 112-20.
Emery, J.D., et al., Accuracy of SIAscopy for pigmented skin lesions encountered in primary care: development and validation of a new diagnostic algorithm. BMC Dermatol, 2010. 10: p. 9
Fisher, R.A., The use of multiple measurements in taxonomic problems. Annals of Eugenics, 1936. 7: p. 179-188.
Fix, E. and J.L. Hodges, Discriminatory Analysis, nonparametric discrimination: Consistency properties. 1951.
Friedman, J.H., Multivariate Adaptive Regression Splines. The Annals of Statistics, 1991. 19(1): p. 1-67.
Friedman, J., T. Hastie, and R. Tibshirani, Regularization Paths for Generalized Linear Models via Coordinate Descent. Journal of Statistical Software, 2010. 33(1):1-22
Friedman, Robert J., et al., The Diagnostic Performance of Expert Dermoscopists vs a Computer-Vision System on Small-Diameter Melanomas, Arch Dermatol. 2008;144(4):476-482.
Henning, J. Scott, et al., The CASH (color, architecture, symmetry, and homogeneity) algorithm for dermoscopy, J Am Acad Dermatol 2007;56:45-52.
Hofner, B., et al., Model-based boosting in R: a hands-on tutorial using the R package mboost. Computational Statistics, 2012. 29(1-2): p. 3-35.
IBM detects skin cancer more quickly with visual machine learning. Computer World News; Available from: http://www.computerworld.com/article/2860758/ibm-detects-skin-cancer-more-quickly-with-visual-machine-learning.html.
Malvehy, J., et al., Clinical performance of the Nevisense system in cutaneous melanoma detection: an international, multicentre, prospective and blinded clinical trial on efficacy and safety. Br J Dermatol, 2014. 171(5): p. 1099-107.
Memorial Sloan Kettering Trains IBM Watson to Help Doctors Make Better Cancer Treatment Choice 2014; Available from: https://www.mskcc.org/blog/msk-trains-ibm-watson-help-doctors-make-better-treatment-choices.
Menzies, S.W., et al., The performance of SolarScan: an automated dermoscopy image analysis instrument for the diagnosis of primary melanoma. Arch Dermatol, 2005. 141(11): p. 1388-96.
Monheit, G., et al., The performance of MelaFind: a prospective multicenter study. Arch Dermatol, 2011. 147(2): p. 188-94.
Nachbar, F., et al., The ABCD rule of dermatoscopy. High prospective value in the diagnosis of doubtful melanocytic skin lesions. J Am Acad Dermatol, 1994. 30(4): p. 551-9.
Otsu, N., A threshold selection method from gray-level histogram. IEEE Transactions on System Man Cybernetics., 1979. SMC-9(1): p. 62-66.
Ramezani, M., et al., Automatic Detection of Malignant Melanoma using Macroscopic Images. J Med Signals Sens, 2014. 4(4): p. 281-90.
Rigel, D.S., et al., The evolution of melanoma diagnosis: 25 years beyond the ABCDs. CA Cancer J Clin, 2010. 60(5): p. 301-16.
Rokach, L., Ensemble-based classifiers. Artificial Intelligence Review, 2010. 33: p. 1-39.
Rosipal, R. et al., Overview and Recent Advances in Partial Least Squares, in Subspace, Latent Structure and Feature Selection, C. Saunders, et al., Editors. 2006, Springer Berlin Heidelberg. p. 34-51.

(56) References Cited

OTHER PUBLICATIONS

Sgouros, D., et al., Assessment of SIAscopy in the triage of suspicious skin tumours. Skin Res Technol, 2014; 0:1-5.

Vestergaard, M.E., et al., Dermoscopy compared with naked eye examination for the diagnosis of primary melanoma: a meta-analysis of studies performed in a clinical setting, British Journal of Dermatology 2008 159, pp. 669-676.

Wolf, J.A. et al., Diagnostic inaccuracy of smartphone applications for melanoma detection—reply. JAMA Dermatol, 2013. 149(4): p. 422-426.

Extended European Search Report for EP Application No. EP14829442.4 dated Mar. 2, 2017.

Office Action for Japanese patent application No. 2016-529829 dated May 22, 2018.

Office Action for Chinese patent application No. CN201480052009.5.

\* cited by examiner

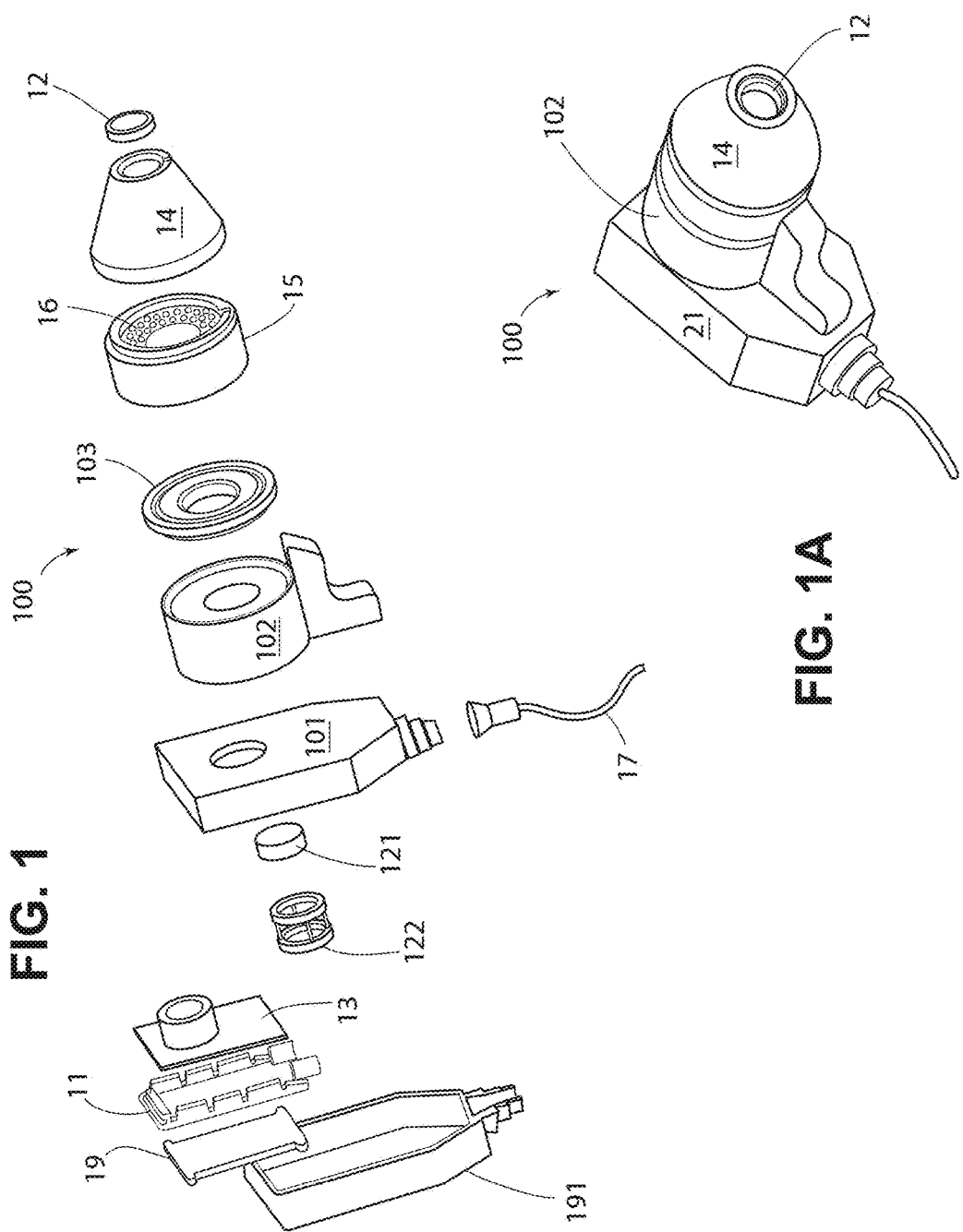

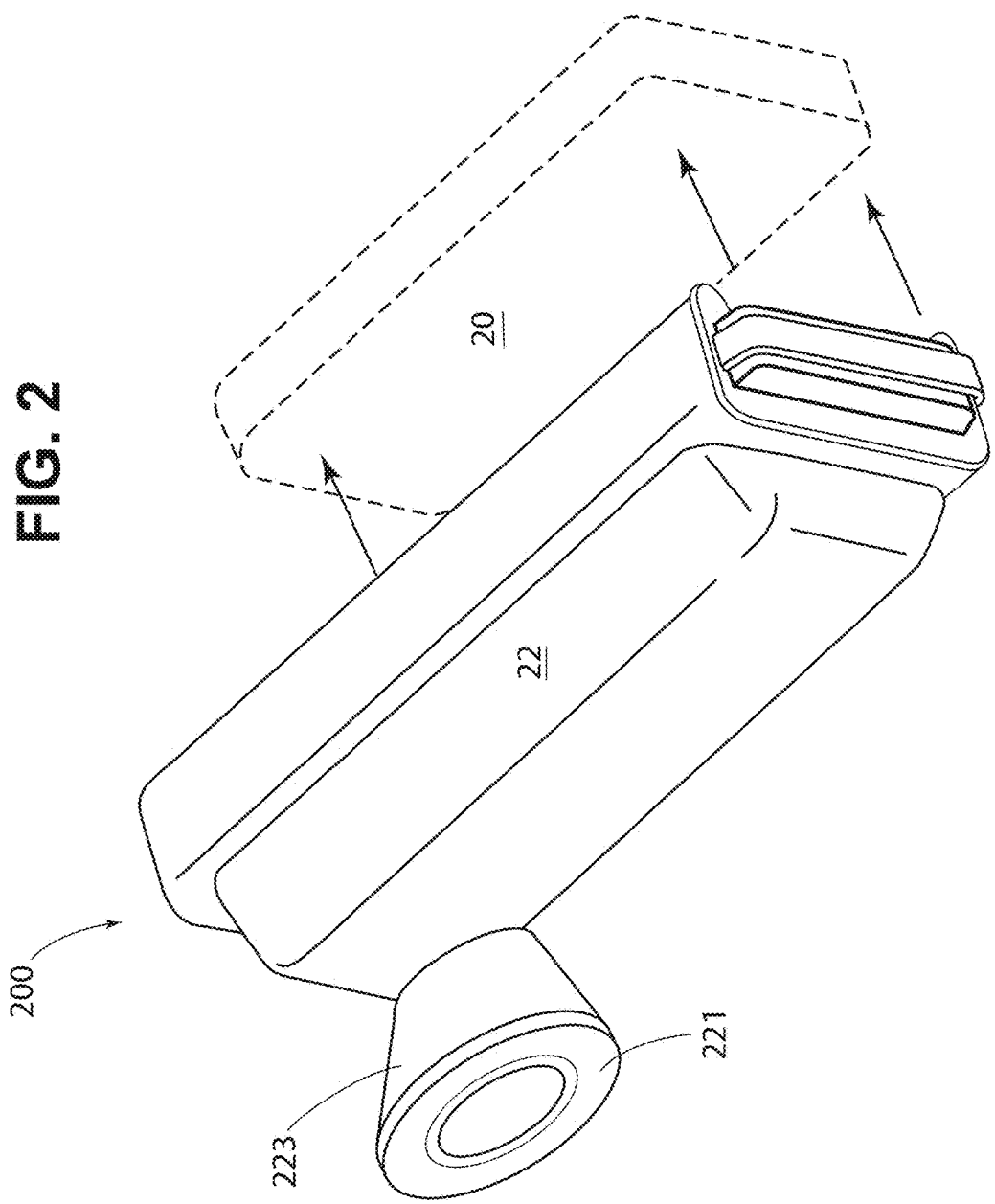

SYSTEM AND METHOD FOR OPTICAL DETECTION OF SKIN DISEASE

This application claims the benefit of U.S. Provisional Application No. 61/857,143, filed Jul. 22, 2013, which is incorporated by reference.

BACKGROUND OF THE INVENTION

Field of the Invention

The invention is directed to systems and methods for optical detection of skin disease and in particular apparatus and methods adapted to detect the presence of melanoma and to distinguish, for example, malignant melanoma from non-malignant dysplastic nevi and/or common nevi, using metrics and classifiers obtained from rotational analysis of image data obtained from a subject's skin lesion. The data obtained may be processed by one or more computer processors and output in a plurality of display modules.

Description of the Related Art

Melanoma, the most lethal skin cancer, incurs immense human and financial cost. Early detection is critical to prevent metastasis by removal of primary tumors. The early lateral growth phase is a vastly preferable detection window to the subsequent phase of metastatic initiation. Optical detection technologies for automated quantitative metrics of malignancy are needed to more accurately guide decisions regarding the need to biopsy and to make preoperative determination of adequate margins for surgical excision. After invasive biopsy or excision, diagnosis obtained by histopathologic evaluation is nearly 100% accurate; however deciding which lesions to biopsy is challenging. Only 3% to 25% of surgically-excised pigmented lesions are diagnosed as melanomas. Hence there is a need for noninvasive screening mechanisms that are both widespread and more accurate.

Dermoscopy is a common dermatological technique to evaluate skin lesions. The dermatoscope typically consists of a light emitting diode (LED) illuminator, a low magnification microscope, and a clear window surface to flatten the skin against. The use of polarization enables partial rejection of deeply penetrating light, which can enhance superficial features of particular diagnostic interest. A digital imaging camera may also be attached to the dermatoscope.

U.S. Pat. Nos. 7,006,223, 7,027,153, 7,167,243, and 7,167,244 describe handheld dermoscopic epiluminescence devices. As noted above, such handheld devices are available commercially which have been adapted for attachment to a cellular phone camera or portable camera.

Methods and apparatus for evaluating optical image data obtained from a skin lesion on a subject's body are taught in U.S. Pat. Nos. 6,208,749 and 7,894,651, assigned to Mela Sciences, Inc. One of the objects of the present invention is to employ algorithms that perform these evaluations with greater sensitivity, specificity and overall diagnostic accuracy, and which can be used to produce diagnostically relevant quantitative metrics in real time, in some cases without further per lesion evaluation.

Another object of the invention is to combine a dermatoscope, digital camera and automated screening by computer vision to bridge the diagnostic accuracy gap between invasive and noninvasive pathological analyses. Though the sophistication of the human brain may never be matched by computers, the present invention leverages three critical advantages over traditional dermatological screening: standardization, quantification and the enhanced ability to perform brute-force calculations. As outlined in the following description and claims, objective analytical diagnostic technologies have the potential to dramatically improve the diagnostic accuracy of widespread melanoma screening.

Using rotational analysis of image data obtained from a skin lesion yields improved diagnostic accuracy compared to the prior art. The novel mathematical descriptors generated by the polar transformation of the image data may be trained on a set of skin lesions of known pathology to yield classifiers which provide a percent likelihood that a given lesion is malignant melanoma, paired with a percentage uncertainty for the prediction. The invention also provides enhanced opportunities to visualize the data obtained. In addition to a standard red-green-blue (RGB) image of the lesion, the present invention provides the user (doctor or patient) with a version of the image with suspicious regions highlighted, and the user may toggle between these display modes. The user may cycle through a set of gray scale images obtained at different wavelengths. The display may be toggled between x-y coordinates and a brightness map in polar coordinates $(r, \theta)$.

SUMMARY OF THE INVENTION

In one aspect, the invention is an apparatus for detecting skin disease in a lesion on a subject's skin, comprising: a mechanical fixture defining a distal plane against which a lesion on the subject's skin is pressed; a camera adapted to obtain image data from the lesion; a processor adapted to process the image data with a clock-like sweep algorithm to obtain metrics and/or classifiers defining the rotational symmetry of the pigmented lesion; and an output device to indicate a likelihood of the presence or absence of skin disease in the subject obtained from the processed image data.

The clock-like sweep algorithm evaluates the brightness of pixels on a line segment connecting the center of the lesion image with the lesion image border as the line segment rotates around the center of the lesion with one end of the line segment fixed at the center of the lesion image. Rotational symmetry refers to different information obtained on the line segment at different angular positions. Thus, a circle with uniform brightness throughout exhibits perfect rotational symmetry. However, if the distance from the border of the lesion to the center of the lesion is different at different angular positions; or if the brightness of pixels differs at different positions on the line segment, or at different angular positions of the line segment, then the lesion is not rotationally symmetric. The asymmetry may be quantified and used to produce diagnostically relevant metrics.

The camera is adapted to obtain multispectral images, as the skin lesion is illuminated with an array of LEDs that emit light of different spectral profiles (including, importantly, one or more LEDs that emit light in the non-visible UV range, such as 300 nm to 400 nm). The camera acquires M images, storing each pixel in the image as a set of M numbers that form a spectral measurement, which are then fixed as the weighted sum of N chromophores.

In another aspect, the invention is embodied as a method for obtaining an indication of a likelihood of the presence or absence of skin disease in a subject, comprising the steps of obtaining image data from a subject's skin with a camera; and processing the image data with a computer processor adapted to implement a clock-like sweep algorithm to obtain diagnostically relevant metrics and/or classifiers defining the rotational symmetry of a pigmented lesion on the subject's skin. In the method, at least one processor transforms the image data into diagnostically relevant metrics and/or classifiers defining the rotational distribution of [a] the spatial texture features or [b] the brightness features or [c] the features of the edge/border or [d] the color variation of a lesion on the subject's skin or [e] variations in the features of the pigmented network including the length, shape brightness and organization of the lesion segments or [f] the oxygen saturation of the tissue as defined by the amount and ratio of oxyhemoglobin and deoxyhemoglobin.

BRIEF DESCRIPTION OF THE DRAWINGS

FIG. 1 is an exploded view of a clinical apparatus according to one embodiment of the invention.

FIG. 1A depicts the assembled apparatus of FIG. 1.

FIG. 2 depicts a cellular phone having an integrated processor and camera and an attached fixture for mounting the camera against a subject's skin according to another embodiment of the invention.

DETAILED DESCRIPTION OF THE INVENTION

System and Apparatus

Figure 3A:
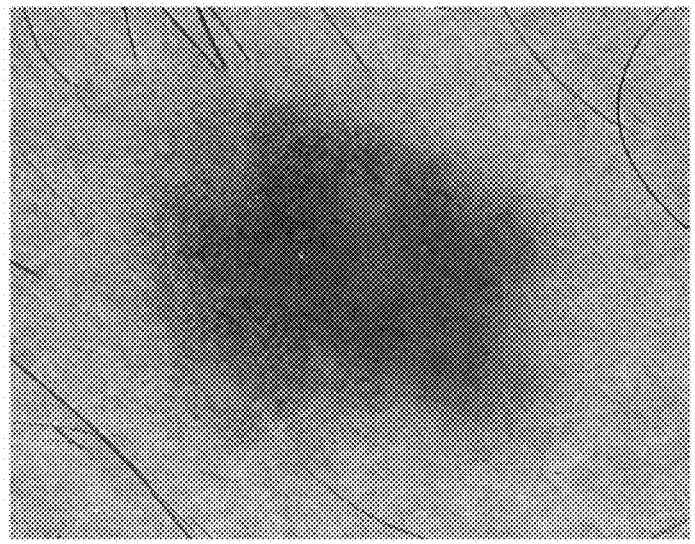
FIG. 3A and FIG. 3B depict the polar transformation of image data for a nevis.

A system according to the invention comprises a camera, a mechanical fixture for mounting the camera in a fixed position with respect to the subject's skin, at least one processor adapted to perform the clock sweep algorithm, and at least one output device.

In the clinical embodiment depicted in FIG. 1, the camera is a circuit board level charge coupled device (CCD) detector imaging array mounted on a fixture that can be pressed against the subject's skin. In this embodiment, the fixture 100 defines a distal plane formed by a flat transparent plate 12 of glass, polycarbonate, polymethylmethacrylate (PMMA) or the like, that may be pressed against the subject's skin so that the lesion stays in one plane when the image is obtained. Plate 12 may be mounted on a spacer, such as nose cone 14, which protects the camera lens aperture and provides an optimal distance between the illuminating and imaging apparatus and the lesion.

An illumination apparatus, such as LED mounting ring 15, positions LEDs around the optical axis of the camera and may be located proximally of the distal plane which frames the skin lesion, but still forward of the imaging apparatus. The illumination apparatus includes a set of devices that emit light of different spectral profiles to illuminate the skin lesion with light at desired wavelengths. In FIG. 1, the LED mounting apparatus comprises a ring of light emitting diodes (LEDs) 16 each capable of emitting light at a specified wavelength in a range of 300 nm to 950 nm while the camera sequentially acquires images at the specified wavelengths. The apparatus may utilize commercially available LEDs which are inexpensive and widely available with various spectral characteristics. However, if more accurate and narrow spectra are desired, laser illumination elements may also be used.

The LED wavelengths are selected based on the methods used to extract relevant information from the image data to identify diagnostically relevant patterns in the lesion. For example, it is known in the art that blue light is absorbed by melanin (one of N chromophores in the skin). Thus, at least one of the LEDs in the array, and preferably a plurality, emit light in the violet-indigo-blue wavelength ranges, 400-500 nm. Blood absorbs in the green, so that at least one of the LEDs in the array and preferably a plurality, emit light centered at the 525 nm wavelength. Pigment at the deepest portion of a lesion, in a relatively deep lesion, has absorption shifted to the red, so that one or more LEDs emit light in the range of 600 nm to 750 nm, and even into the infrared (IR) (780 nm and above) which may be helpful to determine the deepest portion of a lesion to be excised, for example. Illumination in the non-visible ultraviolet (UV) range to obtain information about the skin lesion is another novel aspect of the invention. Thus at least one, and preferably a plurality of LEDs in the array, are adapted to illuminate the skin at a wavelength of 300 nm to 400 nm. At least one, and preferably a plurality of LEDs are adapted to illuminate the skin in accordance with the absorption profile of eu-melanin as distinct from the absorption profile of pheo-melanin. In this way, at each angular position, as the camera acquires M images at different wavelengths, each pixel in the image is stored as a set of M numbers that form a spectral measurement which may be fit as the weighted sum of N chromophores in the skin lesion.

In embodiments, particularly where off-the-shelf LEDs are used, the illumination system may comprise a set of LEDs having illumination spectra that overlap. In this case, correction may be made digitally, providing a processor adapted to remove overlapping regions of the spectra, thereby improving spectral resolution. For example, a set of LEDs may have spectra $L_1, L_2, L_3 \ldots L_n$ that overlap, and image data obtained at one illumination, $I\_L_i$, may be used to correct the illumination at $I\_(L_{i-1})$ by subtracting $C^*(I\_L_i)$ from $I\_(L_{i-1})$, where C is a constant related to the amount of overlap between the two spectra.

This correction may be programmed in advance based on the specifications from the manufacturer of the LED. Alternatively, the apparatus may be provided with a spectrometer to measure the emission spectra of the LED or other illumination device, and that measurement may be used to implement the correction for overlapping spectra. A fiberoptic element located distally of the illumination devices provides the data from the actual emission spectra of each illumination device to the processor to perform the steps described above for resolving the overlapping spectra.

Housing 101 comprises one or more lenses 121 mounted in the mechanical fixture 122 between the camera 13 and the distal plane 12 to focus the camera on the distal plane, and may comprise one or more filters, such as a polarizing filter or chromatic filter to condition the light emitted by the LEDs or reflected by the lesion and captured by the camera. The lenses are designed to minimize optical aberrations and maximize optical transport throughput at the wavelengths of the illumination light.

The processing functions may be shared between first and second processors. The first processor is typically an onboard processor such as circuit board 11 adapted to drive the camera and illumination system to acquire the image data and provide a real time information display to the user. The first processor may transmit image data to a second processor adapted to perform data-intensive processing functions which cannot readily be provided as real time display. The second processor may deliver messages back to the first processor for display. The second processor, if present, is typically a remote processor. The second processor may create data files, image files, and the like, for later use.

In FIG. 1, the first processor is circuit board 11, adapted to drive the camera and the illumination of the LEDs, while the camera sequentially obtains M images at the selected wavelengths. The first processor may process the image data so obtained to produce a display on a liquid crystal display ("LCD") view screen 19. Outer housing 191 encloses the LCD screen and circuit board. Cable 17 is used to attach a second processor and other components to the apparatus.

As shown in FIG. 1A, fixture 100 is provided with a lens holder 102 attached to the nose cone by a spacer 103, sized to provide a self-contained assembly that can be manipulated with one hand and positioned against a subject's skin lesion.

Provided sufficient image data are obtained at different wavelengths, diagnostically relevant areas of interest on the skin lesion may be identified and differentiated using a variety of display modules. Thus, colors correlating to blood vessels within the lesion border; colors correlating to blue and blue white structures in the lesion; colors correlating to pigmented networks which may be regular or irregular; colors correlating to negatively pigmented networks; patterns of oxygen saturation; and patterns of eumelanin and pheomelanin (which have different absorption profiles) all may be highlighted and separately displayed with the display modules described below.

Figure 4:
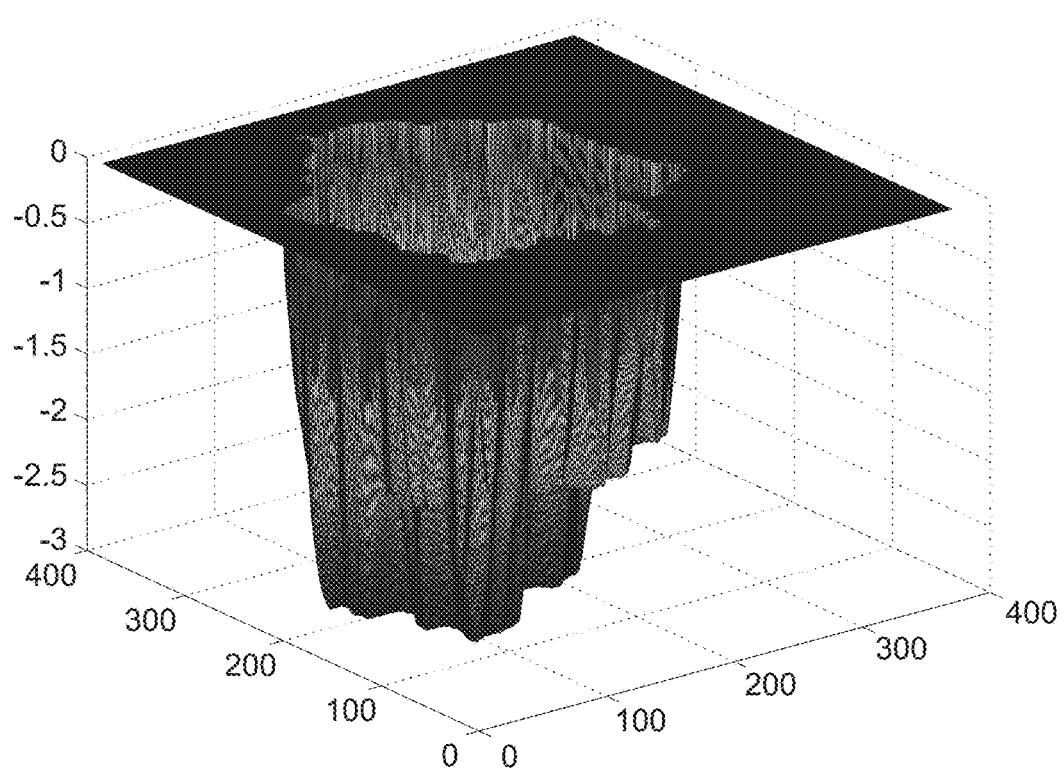
FIG. 4 is a topographical map of a lesion constructed from mask images according to a display module in one embodiment of the invention.

The processor(s) is adapted to transform the image data into diagnostically relevant metrics and/or classifiers indicating the likelihood of disease or presence or absence of features such as those identified above by defining [a] the spatial texture features or [b] the brightness features or [c] the features of the edge/border or [d] the color variation of a lesion on the subject's skin or [e] variations in the features of the pigmented network including the length, shape, brightness and organization of the lesion segments or [f] the oxygen saturation of the tissue defined by the amount and ratio of oxyhemoglobin and deoxyhemoglobin, and these characteristics may be displayed in one or more display modules to render a version of the lesion image depicting the lesion, or segments of the lesion, with one or more of these features of interest highlighted on a display for the user. In one display module, depicted in FIG. 4, the N spectral images are processed to form a topographical map of the lesion pigment from mask images obtained at each of a plurality of specified wavelengths. A mask image is defined as an image having pixel brightness 1 inside the image border and 0 outside the image border. Image data obtained at each of the plurality of wavelengths will yield a different mask image. Adding mask images at different wavelengths permits the construction of a topographical map. FIG. 4 is a black and white rendering of an original color image. This display module, which approximates a three-dimensional display, may be useful to identify the appropriate excision borders for a skin lesion.

Figure 5:
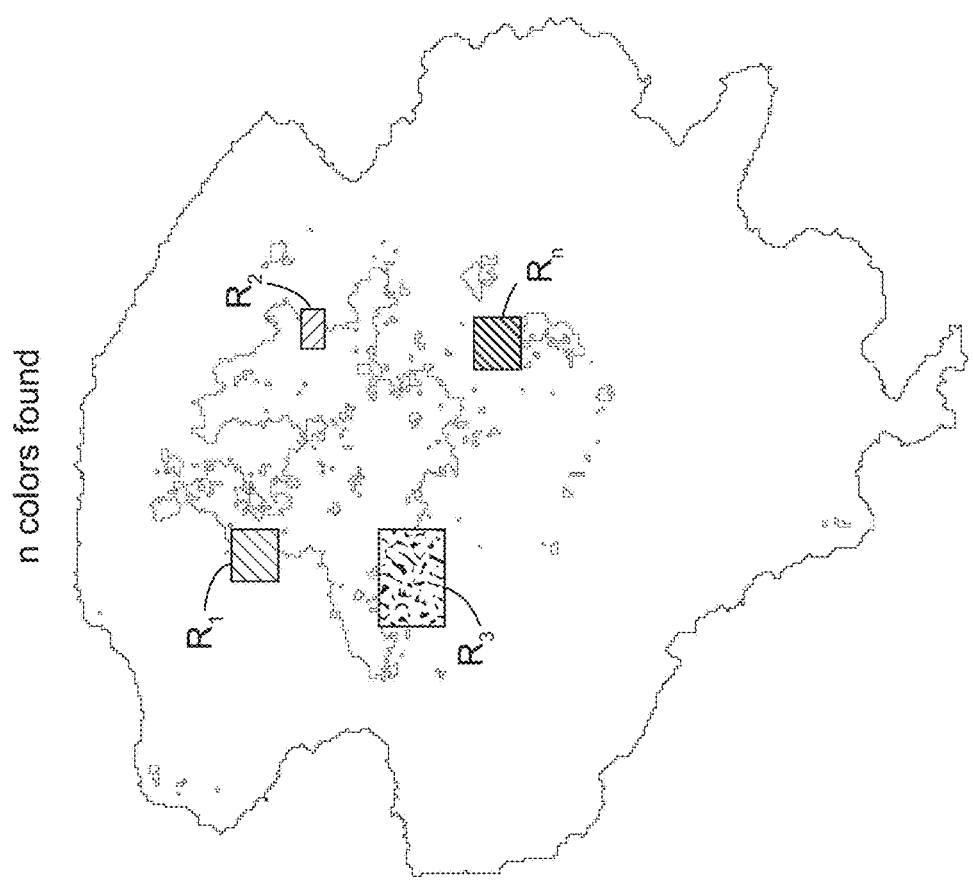
FIG. 5 is a schematic view of a solid false color display according to a display module in another embodiment of the invention.

In another display module depicted in FIG. 5, the N sequential images obtained by the camera are processed to render a display of the lesion in which areas of interest in the lesion are shown in solid "false color." The solid false colors in the display, for example, light brown, dark brown, red, black, blue/gray, and white, may be counted and the number of colors displayed. The solid false colors may correspond to detected regions of interest in the lesion, such as a region consisting of blood vessels within the lesion border; blue or blue-white skin structures a pigmented network that is labeled as regular or irregular; negative pigmented network (a pattern of lightly pigmented skin within the lesion borders); and an abnormal pattern of oxygen saturation as defined by spectral fitting using near-infrared wavelength illumination. The display may toggle between a color image created from the N spectral images and the same image with a region or regions of interest indicated at the selection of the user. The highlighted features $R_1, R_2, R_3 \ldots R_n$ are depicted schematically in FIG. 5 as rectangles. In an actual embodiment, the shape of these highlighted features corresponds to the shape of the underlying feature in the skin lesion.

Figure 3B:
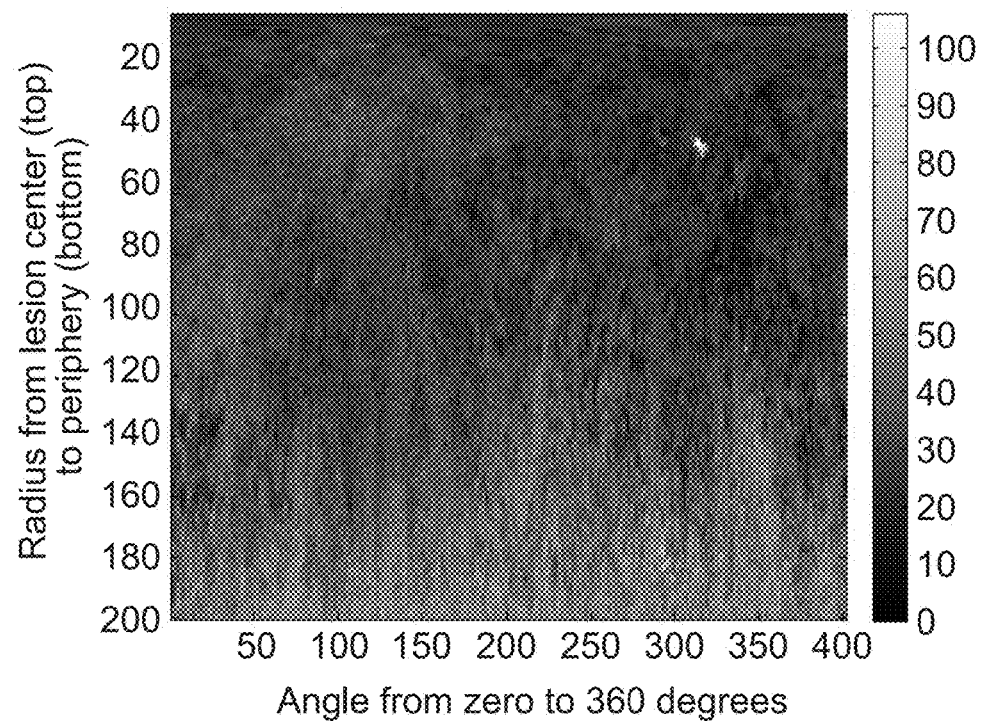
Figure 3C:
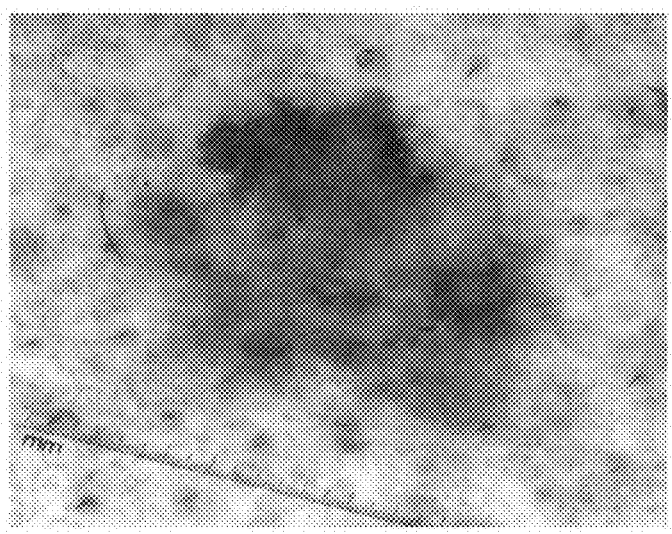
FIGS. 3C and 3D depict the polar transformation of image data for a malignant melanoma.
Figure 3D:
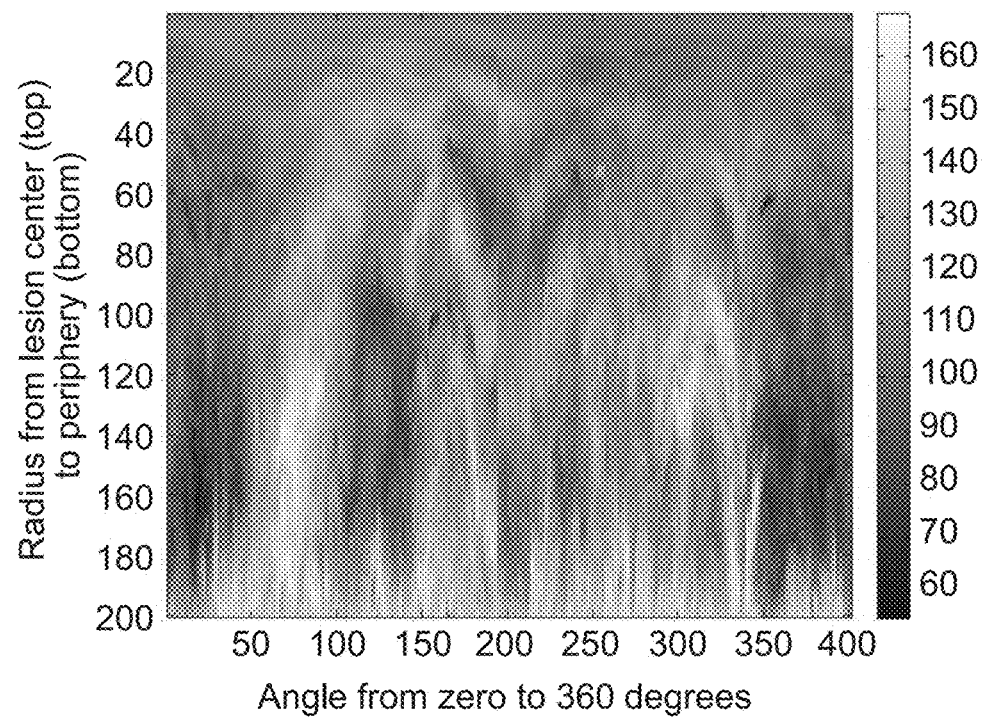

The display module of FIGS. 3A through 3D depicts the analytical advantage of the polar transformation of the visual data obtained from a skin lesion according to the present invention. FIG. 3A depicts conventional image data of a non-malignant skin lesion at a given wavelength. FIG. 3B depicts the polar transformation of the image data from FIG. 3A, in which the x-axis represents an angular position of the sweeping arm, and the y-axis represents the brightness values along the sweeping arm at each angular position. FIG. 3D depicts the same transformation of the image data from FIG. 3C, where the underlying image data is from a malignant melanoma. This display module provides a visual impression of the brightness variation in the malignant skin lesion, which is much greater than the variation in brightness of the non-malignant lesion. Even before quantitative evaluation, presentation of this image data in polar coordinates provides a new vantage to view a clinically relevant metric.

Figure 11:
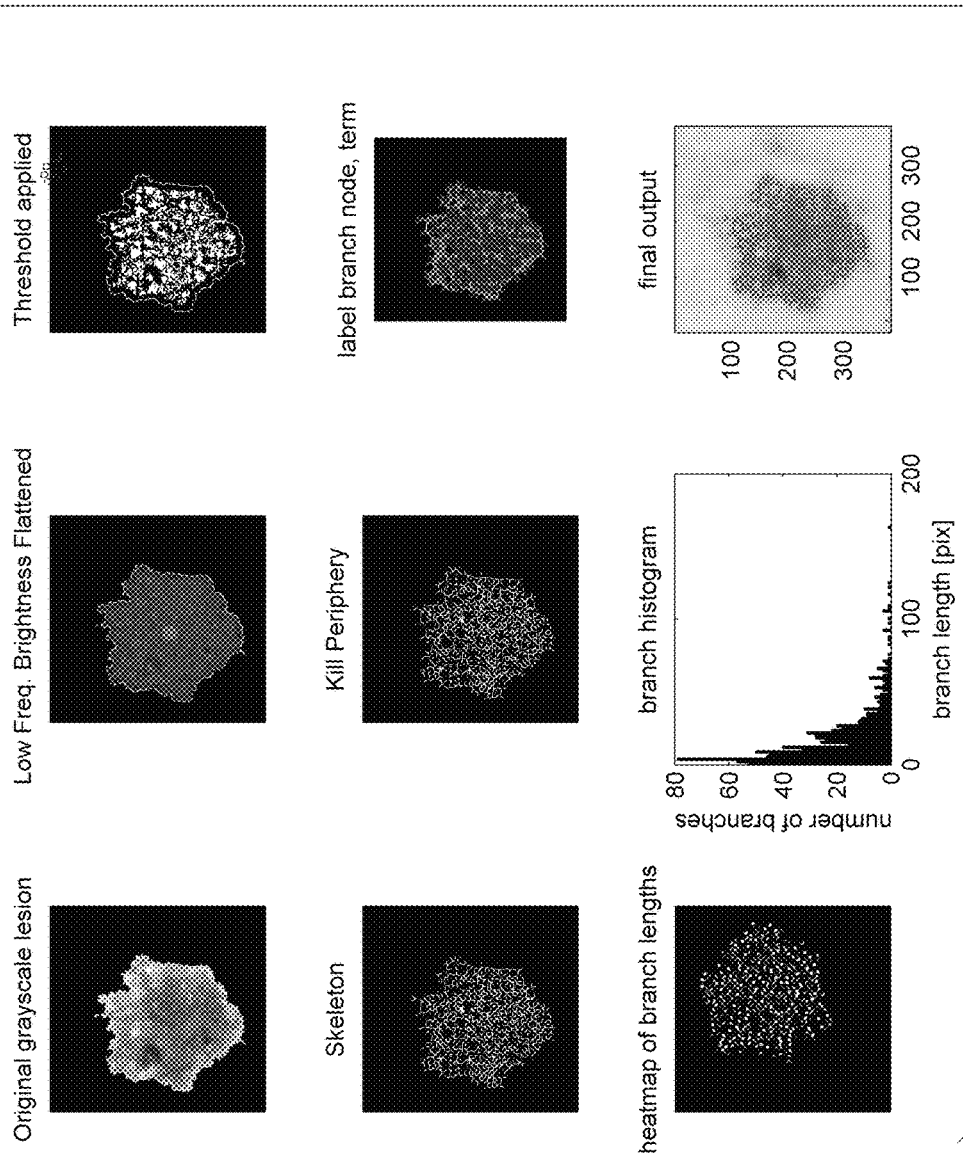
FIG. 11 depicts a transformative process performed on image data from a skin lesion to obtain a metric relevant to the pigmented network regularity in a skin lesion.

FIG. 11 depicts a series of data transformation steps which identify network nodes and branch segment lengths in skin lesion image data and provides a metric of network irregularity. In this context, "regular or irregular pigmented networks" refers to a measure of regularity defined by the branch segments of the network in terms of the length and width of each branch segment and the collective angular variation of those values. Important metrics are generated by identifying and characterizing pigmented networks from the image data, including the steps of: a) identifying branch segments; b) locating the coordinates of the centroid of the branch segment; c) determining the length and width of the branch segment and the ratio of length to width (or other mathematical combination of length and width); d) determining the brightness of the segment; e) determining the variation in brightness of the segment over different illumination wavelengths, $I\_L1, I\_L2, I\_L3 \ldots I\_Ln$; f) determining the number of nodes (where two branch segments meet), the number of ends, and the ratio of the number of nodes to the number of ends (or other mathematical combination of the nodes and ends).

In identifying pigmented networks, especially to distinguish a pigmented network from a blood vessel structure, the variation in brightness across wavelengths is useful, because the blood vessel structure absorbs at different wavelengths than the pigmented reticular structure.

The ratio of length to width is used to differentiate globular pigment patterns (where the ratio is closer to 1), from reticular patterns (where the ratio is much greater than 1). Variation in the ratio across the angular sweep produced is another metric correlated with melanoma.

The ratio of the number of nodes to the number of ends produces a metric correlated with melanoma because a broken network (i.e., a lower node:end ratio) indicates melanoma.

In addition to LCD viewer 19, the apparatus may comprise additional display outputs, adapted to display the M black-and-white or color coded scale images taken at M wavelengths as views in sequence or in a selectable manner, which may be facilitated by a server application between a computer and the data acquisition device. Data analysis of the multispectral imaging described herein was performed in the Matlab environment. However, transferring these program elements to a different programming platform is within the skill of one having ordinary skill in the art and this transfer is contemplated for commercial applications.

The camera may also be controlled with a server application that facilitates the image acquisition process and which can be operated independently or controlled through any separate software system capable of file input and output and simulating keystrokes. The server application acts as a bridge between the data gathering process and the data analysis code, to power the LEDs that illuminate the sample, to send image acquisition triggers to the camera, and to receive image information from the camera for data analysis in an efficient manner. The server application works by waiting for keystrokes (real or simulated) using a Windows message loop, which it then interprets and uses to send different commands to the camera. Additional data transfer between the server application and third party programs is accomplished using standard file input/output ("I/O") functions.

This server may be developed as a console application in C++ computer language, for example, with the ability to be re-implemented as a windows application, to handle image acquisition and changing resolution, exposure time and gains settings with the ability to add additional functionality as necessary. By enabling the server to be controlled by keystrokes, it can be used on its own to acquire images from the camera or in conjunction with third party applications that can simulate keystrokes. Total acquisition time for imaging 14 different wavelengths of light can be reduced to about 30 seconds or less (as opposed to around 60 seconds using software provided by the camera manufacturer). This server also enables a live feed display, enabling the user to position the assembly 100 around a suspicious lesion, for example, with a frame rate of at least 1.3 frames/second. Additional features may be included in the script to prevent accidental keyboard input from interfering with the server application while it is being controlled by a third-party application.

The functionality of the server application is enhanced by code that controls the lighting process, allowing for images to be taken at different wavelengths of light and with exposure times individually suited to each wavelength, as well as code that enables the images to be displayed as a live feed either on a monitor or on a small screen attached to the imaging device.

Figure 10:
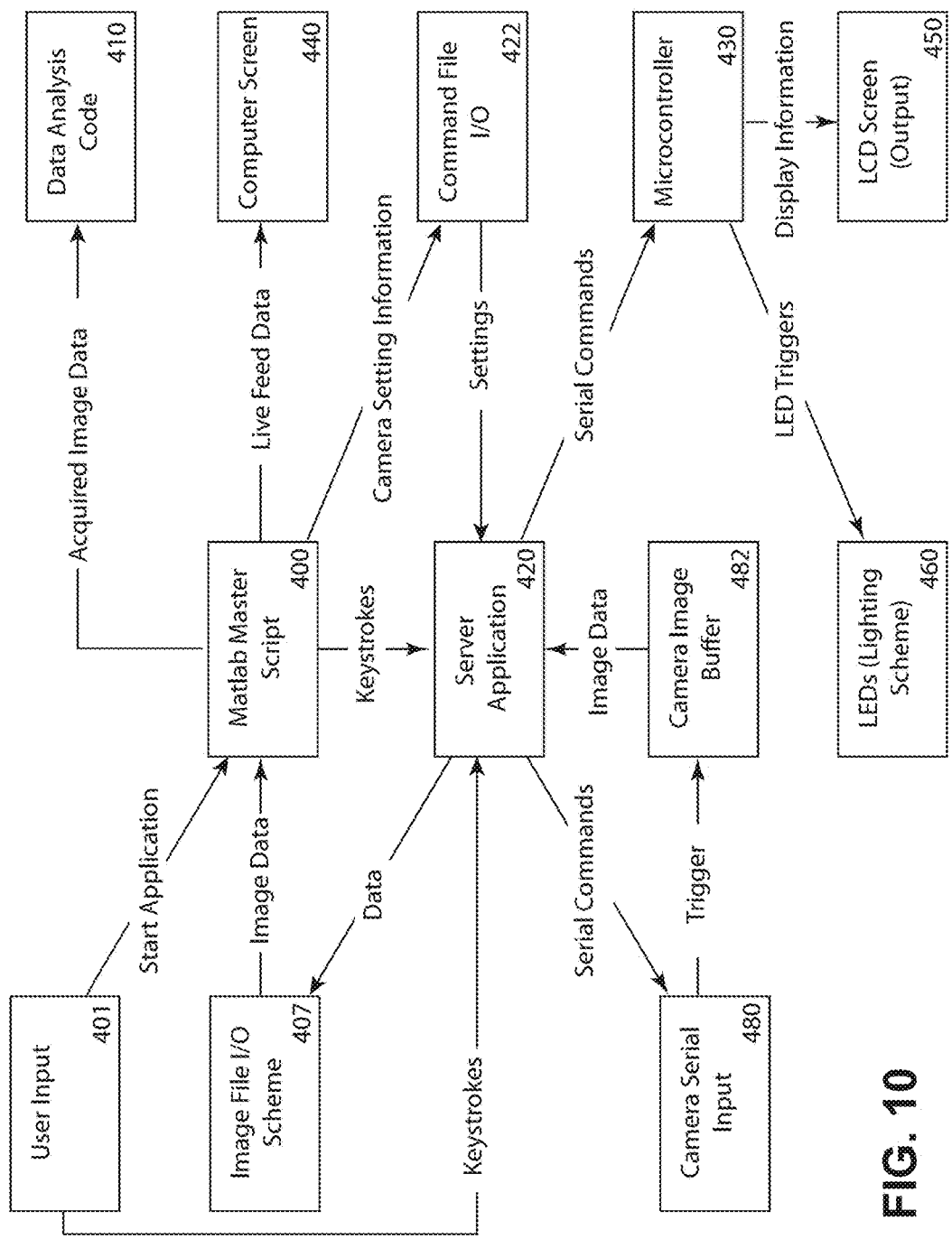
FIG. 10 is a flow chart depicting the operation of a server application controlling the image acquisition and data analysis process according to one embodiment of the invention.

The flow chart of FIG. 10 depicts the flow of commands and data acquisition and analysis using the server application. A master script 400 running on a first computer provides actual or simulated keystrokes to the server application 420, which controls image acquisition triggers through camera serial input 480 and then accesses camera image buffer 482 to return image data to the server application. The server application powers the LED array 460 through microcontroller 430. Once obtained, image data is processed by the master script in a data analysis code module 410. The server application 420 provides data to drive LCD screen output 450 and provides the master script 400 with live feed data for display on the computer screen 440 of the first computer.

In the embodiment depicted in FIG. 2, the camera and processor are integrated in a cellular phone 20 (which includes "smart phones"). Many commercially available cellular phones have adequate camera capabilities and processing capabilities to implement the methods according to the invention. Cellular phones sold under the iPhone® and Android® brands, and many others, have the capability to download server applications to implement the methods described herein.

According to the embodiment of FIG. 2, a mechanical fixture 22 is attached to the cellular phone so that the camera can be securely mounted while the fixture is pressed against the subject's skin. The distal end of the fixture 22 resembles a dermatoscope, and defines a plane 221 against which the subject's skin lesion is pressed to obtain an image while the camera is held in a fixed position. The fixture 22 may include an illumination system in the distal portion 223 of the fixture including an array of LEDs similar to the CCD camera embodiment described above, and/or polarizing or chromatic filter to enable partial rejection of the illuminating wavelengths. In this case, the fixture may be adapted to disable the camera's built-in flash. Alternatively, the processor may be adapted to utilize the built-in flash system provided with the cellular phone.

As with the clinical apparatus, external server applications may be adapted to drive the camera provided with the cell phone and external illumination systems. The cellular phone or smart phone generally has a screen which serves as the output device which provides the user with an indication that a skin lesion is melanoma. The output may take the form of a percentage likelihood that a skin lesion is melanoma, together with a percentage uncertainty, or the program may provide the user with a qualitative message, such as "suspicious lesion: see your dermatologist."

Methods, Metrics and Classifiers

The methods according to the invention may be described as a series of conceptual "steps." As would be apparent to the person of ordinary skill in the art, the steps may be followed sequentially, or in an order different from the order stated; the steps may be done in parallel, done at the same time, or done iteratively, without departing from the scope of the invention. Describing a step as the "first step" or "next step" is for convenience only. The image data obtained from a subject's skin lesion may be manipulated by computer according to these steps and output to display modules.

The first step of the method consists of obtaining image data from a subject's skin with a camera. Generally, this means photographing a lesion on the skin. The resulting image data will comprise data from the lesion and the surrounding skin, and may include data which are not part of the lesion or surrounding skin, including hair, markings made by a dermatologist or other data elements that are not analyzed and simply need to be removed from the image. To complete this step, the processor may replace pixel brightness and color values of the hair-containing locations with pixel brightness and color values of the skin underlying or immediately adjacent the hair, for example.

The image data consists of pixel gray-scale or brightness information in M different color layers. As used herein, a "multispectral image" is an image obtained at a plurality of wavelengths or "layers," so that each pixel in the image is associated with M numbers that form a spectral measurement, and each $m_i$ is a brightness or gray scale measurement at a different color layer. Thus, the image data consists of M images sequentially acquired by the camera while illuminating the skin at wavelengths that range from 300 nm to 950 nm. The spectral measurement is fit as the weighted sum of N chromophores, corresponding to the number M of images obtained. Typically, pixel brightness information is obtained at least in the red-green-blue ("RGB") layers, but pixel brightness information is also preferably obtained for other spectral bands. Relevant information is obtained using illumination and detecting reflected light in the visible and non-visible range, including the blue and UV range at 300 nm to 500 nm, and even more particularly in the non-visible 300 nm to 400 nm UV range.

As used herein, "chromophores" refers to color components found in a skin lesion, such as melanin, oxygenated hemoglobin and deoxygenated hemoglobin. Generally, at least these three have distinct absorption profiles such that the spectral images can be analytically fit as the weighted sum of at least these three chromophores. However, skin contains water, which absorbs in the UV, bilirubin, which has a distinct absorption in the visible spectrum, and potentially could be found to contain other diagnostically relevant components, such that a measurement could be fit as a weighted sum of N chromophores, wherein N is 4, 5, 6, or more chromophores.

Once the image data is obtained, the shape and center of the lesion are identified. The first step in determining the shape is known as "segmenting" and various computer implemented techniques known in the art may be used to identify the shape and border of a lesion. Briefly, segmenting results in a mask being applied so that pixel brightness at a given wavelength is reduced to a mask image, in which pixels have brightness value of 1 inside the lesion and 0 outside the lesion. A "mask" as used herein is an image having a brightness value of 1 inside the image border and 0 outside the image border.

In a subsequent step, the center of the lesion (or close approximation of the center) is determined. The center of the lesion may be calculated as the center of mass or geometric centroid of the mask image, such that each region of the lesion shape is treated as having identical density. Alternatively, the center of mass may take into account the variation of brightness in the shape. Unless stated otherwise, in the following examples, the center of mass is obtained from a mask image, such that the lesion is treated as having uniform brightness to determine the center of mass. As the image will have a different mask and therefore a different border at each wavelength, the image at each wavelength may be associated with a respective center, and the distance between the "centers" ("$\Delta r$") may be used with other metrics. The variance ("var $\Delta r$"), range ("range $\Delta r$") and mean ("mean $\Delta r$") may also be combined into classifiers.

Figure 7:
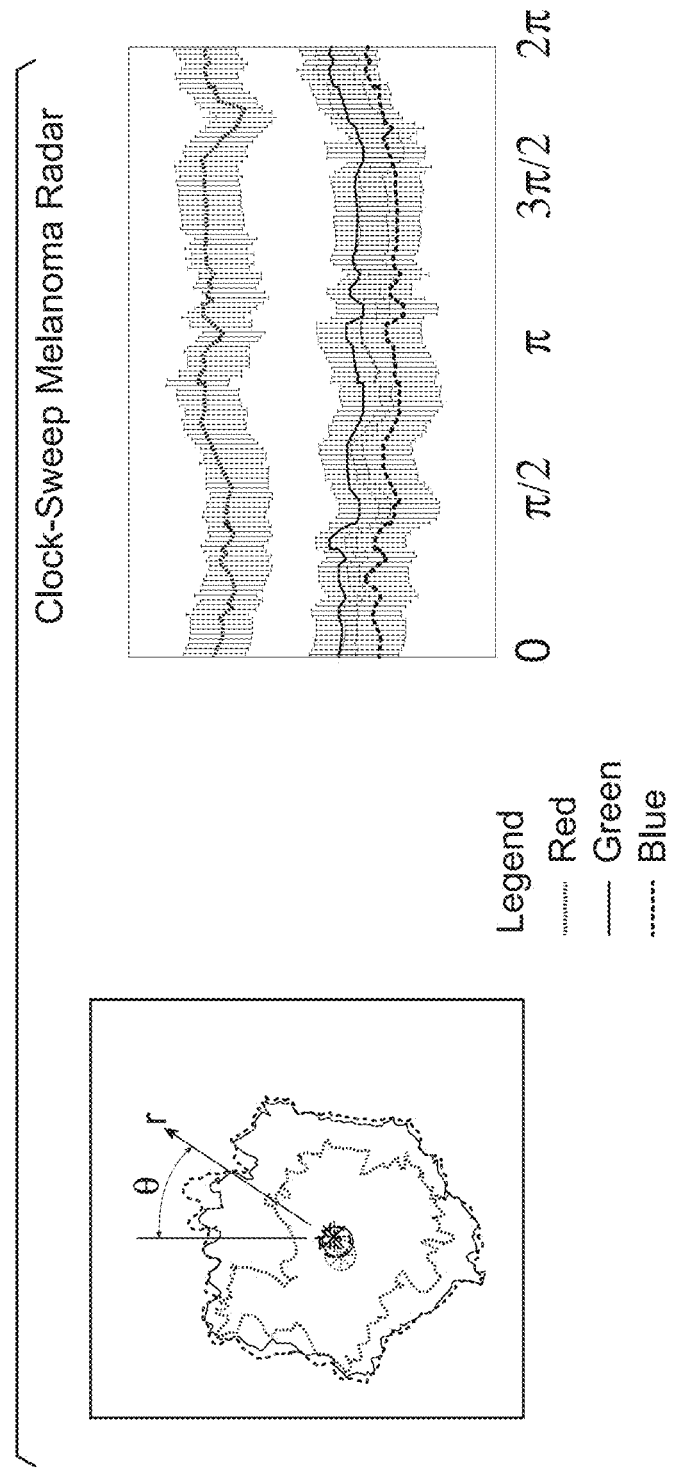
FIG. 7 depicts another display module according to the invention.

A sweeping arm is a line segment connecting the center of the lesion to the border. The "clock-like" sweep as used herein, means rotating the sweeping arm about the fixed center of the image in either a clockwise or counter-clockwise direction to obtain information about the pixels on the sweeping arm as a function of rotation angle. To obtain metrics from the image data, the sweeping arm rotates around the center with one end fixed at the center for 2 pi ($2\pi$) radians or 360° (one complete sweep). Data is sampled at regular intervals of radians or degrees. FIG. 7 depicts the clock sweep arm r at an angle $\theta$ with respect to the vertical. On the left hand side of FIG. 7, borders of the lesion at three different wavelengths are shown. On the right hand side of FIG. 7, the brightness of the pixels on the sweeping arm is plotted as a function of angular position. The data obtained in the sweep may be processed into a series of metrics and/or classifiers which cannot be obtained by evaluation of image data which have not been transformed into polar coordinates.

As used herein, "metrics" are values calculated from the image data which bear a correlation to disease states (melanoma in the preferred examples). Correlations of metrics to disease states may be obtained from a sample of lesions obtained from human subjects containing melanoma and nevi and applying two-sided unpaired t-tests. Table 1 below tabulates P-values for preferred metrics in two-sided unpaired t-tests applied using the methods of the invention to a sample including melanoma and non-cancerous nevi (n=115 samples).

TABLE 1

| | | |
|---|---|---|
| V1 | Angular brightness range | 0.00405135 |
| V2 | Mean standard deviation (S.D.) of brightness | 0.00076328 |
| V3 | Range in S.D. of brightness | 0.00216321 |
| V4 | Standard deviation (S.D.) of S.D. in radial brightness over all angles | 0.00010983 |
| V5 | Mean absolute brightness shift between successive angular positions | 3.96E−05 |
| V6 | S.D. of absolute brightness shifts | 0.00065462 |
| V7 | Sum of the brightness shifts over full sweep | 3.96E−05 |
| V8 | Maximum border asymmetry | 0.25013811 |
| V9 | Border asymmetry evaluated at 90° with respect to the minimum asymmetry axis | 0.81368149 |
| V10 | Lesion border length/lesion area | 0.13076045 |
| V11 | Mean lesion demarcation (edge slope) | 0.00954458 |
| V12 | S.D. of lesion demarcation | 0.62700467 |
| V13 | Fractal dimension | 0.08774601 |
| V14 | Lesion brightness variation over all lesion | 0.19014081 |
| V15 | Mean demarcation (edge slope) fit error | 0.00075154 |
| V16 | S.D. demarcation (edge slope) fit error | 0.04725435 |
| V17 | Lesion brightness variation over all lesion | 0.4408405 |
| V18 | Mean length/area of pigment segments | 0.09845662 |
| V19 | S.D. length/area of pigment segments | 0.10489129 |

Metrics V1 through V7 and V14 capture measurements and statistical information relating to the variation in brightness of pixels on the sweeping arm in relation to other pixels on the sweeping arm, and over different angular positions of the sweeping arm. Metrics V8 through V13 and V15 through V19 capture measurements and statistical information relating to the edge characteristics and presence of reticulated structures in the lesion.

One metric that may be obtained from the angularly sampled data is the angular brightness range (V1), defined as the maximum value of mean brightness on the sweeping arm minus the minimum value of mean brightness over the full rotational sweep. Thus, the mean brightness of the pixels on the sweeping arm is calculated at each angular sample position of the sweeping arm, and the minimum value calculated is subtracted from the maximum value to obtain V1.

The right hand side of FIG. 7 depicts the angular brightness range of pixels on the sweeping arm (V1) as a function of angular position. The mean standard deviation of brightness (V2) of pixels on the sweeping arm is depicted as the vertical line associated with each angular position. Large variations in V1 and a large range of V2 correlate to melanoma. Another metric that may be obtained is the range in standard deviation of brightness (V3). A standard deviation is obtained from all the values of brightness on the sweeping arm at each angular position and the range of these values over all angular positions is calculated to obtain (V3). Another metric is the standard deviation over all angles of the standard deviations at each angular position (V4).

Other metrics evaluate the brightness shift (absolute value) at successive angular positions (V5), the standard deviation of the absolute value of the brightness shift over all angular positions (V6), and the sum of the brightness shift (absolute value) over all angular positions (V7).

The person of ordinary skill in the art of computer-implemented diagnostic analysis of dermoscopic images will recognize that the angularly sampled spectral image data lend themselves to mathematical combination and statistical manipulation once the data is obtained, so that the foregoing list of metrics having correlation to disease states is not exhaustive.

Figure 6:
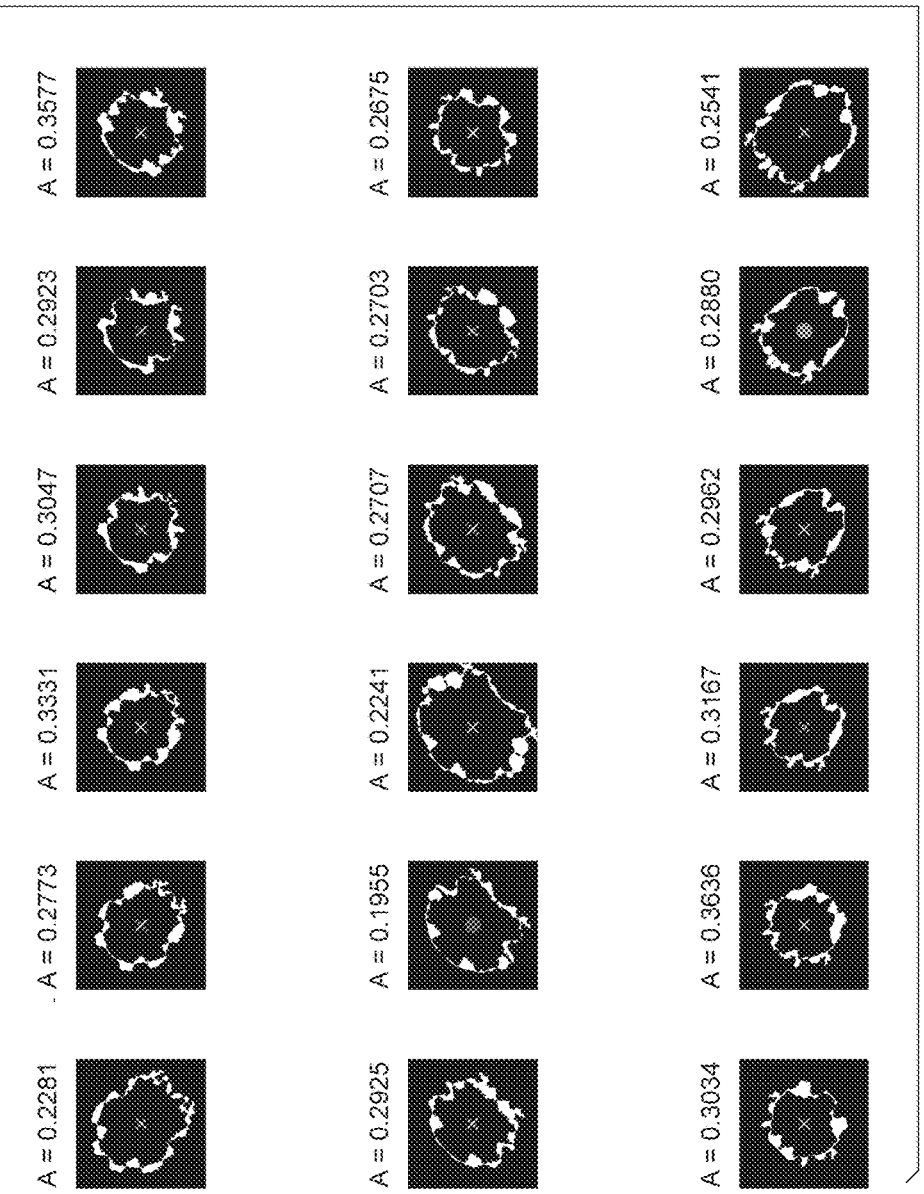
FIG. 6 depicts asymmetry measurements obtained with respect to bisecting axes which are rotated with respect to the image.

The maximum border asymmetry (V8) is another useful metric, along with the border asymmetry perpendicular to the axis of most symmetry (V9). Border asymmetry was obtained by converting the lesion segment in the blue channel to a binary mask and flipping the binary lesion about a bisecting axis. Thereafter, the axis was rotated in 10 degree increments from zero to 180 degrees to obtain 18 samples of asymmetry as a function of analysis axis. The subtraction of the original mask from its flipped counterpart yielded a map where overlapping regions had a zero values (1−1=0), regions not occupied by either the original or flipped mask had zero values (0−0=0) and regions of mismatch had an absolute value of 1 (1−0=1 or 0−1=−1). The absolute value for a perfect circle would be zero everywhere and the sum would be zero, indicating perfect symmetry. Real lesions had mismatched areas, which lead to non-zero values in the subtraction map, which when summed and divided by the sum of just the original mask, equaled the fractional area of mismatch, and represented the asymmetry of the border of the lesion. The angle at which the minimum asymmetry factor occurred was designated as the axis of most symmetry. Then, the asymmetry of the lesion was evaluated at 90 degrees with respect to the symmetry axis. The individual asymmetry images are depicted in FIG. 6.

Some of the metrics obtained from scanning and analysis of the pixel brightness information are obtained for a given wavelength. Other metrics require a combination and/or comparison of image data obtained at different wavelengths. Regions of interest in a lesion may be associated with different colors, including blood vessels (red) within the lesion border, blue or blue-white skin structures, pigmented networks (associated with eumelanin (brown) or pheomelanin (red).

The border roughness metric (V10) is the length of the border of the lesion segment squared divided by the area of the lesion. For a circle, this would be the circumference squared divided by the area.

Initially, the clock sweep may be used to enhance the determination of the border. An edge fit algorithm runs during the clock sweep and utilizes the variation in pixel brightness at the edge of the lesion shape to iteratively determine a more accurate edge.

The "edge slope" metric (V11) is the mean gradient in brightness at the border during the transition from dark (inside the lesion) to light (outside the lesion) over the full sweeping arm rotational range. The standard deviation of edge slope over all angular positions produces the standard deviation of lesion demarcation (V12). An edge fit algorithm may be used to produce a function defining the border of the lesion from the edge slope which also produces edge slope fit error (V15). An edge slope fit error for the standard deviation of lesion demarcation (V16) may be similarly obtained. The fractal dimension (V13) is another measure of the border irregularity which may be calculated according to known methods. The length to area ratio of pigment segments (V18) and standard deviation of this ratio (V19) are also metrics which bear correlation to melanoma.

Figure 8:
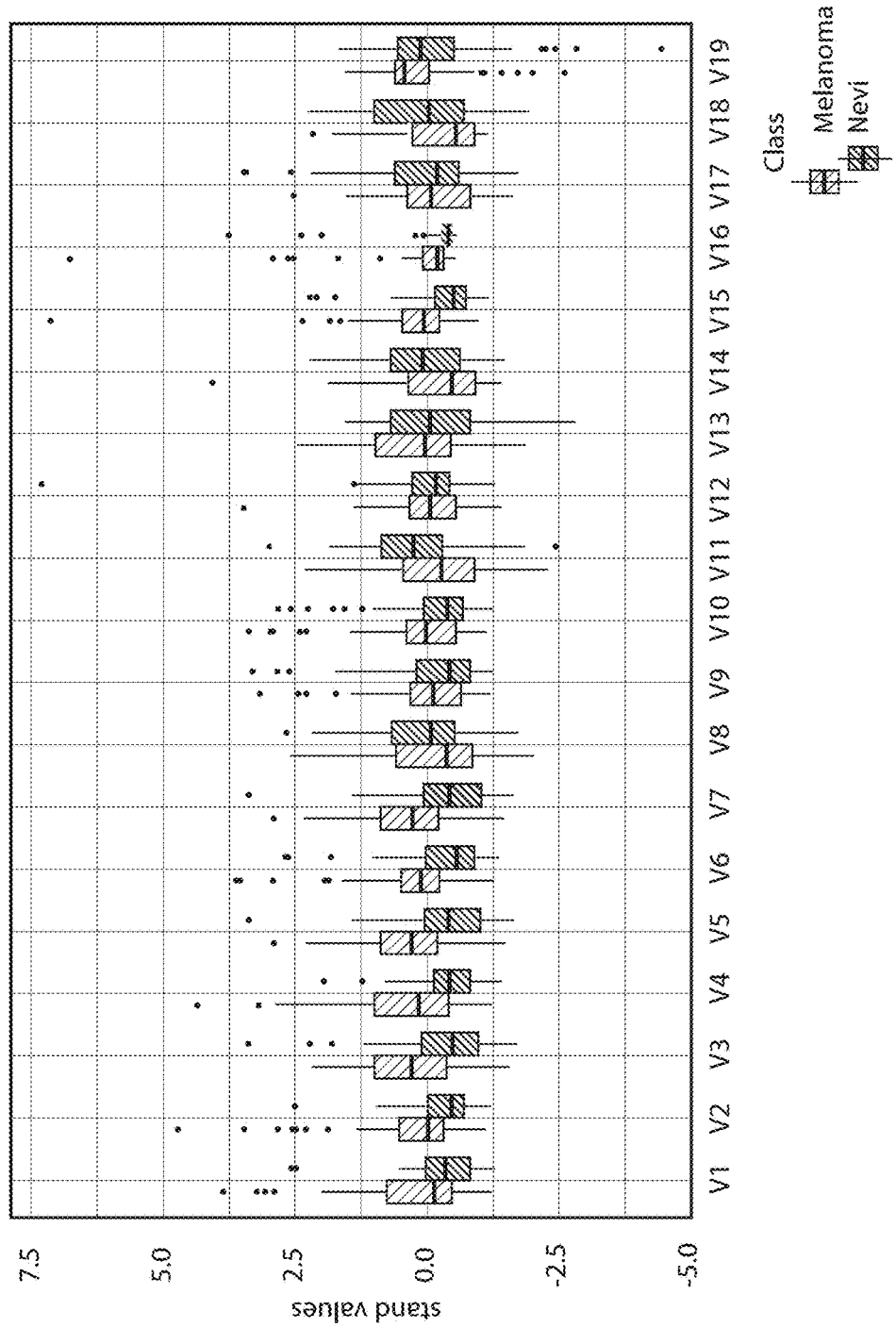
FIG. 8 is a visualization of the discriminative power of metrics used in the method of the invention.

FIG. 8 depicts the discriminative power of each of the metrics V1 through V19. Each box in the chart represents an interquartile range of values for a given metric according to whether the skin lesion in the sample is a melanoma or nevus (as determined by pathologist screening); therefore, each metric is associated with two columns of data points and two boxes. The vertical lines in each column represent barriers for atypical data and the points above and below represent potential outliers. Thus, the larger the vertical displacement of the boxes for nevus and melanoma, the more discriminating the metric. A shorter overall height of the boxes in the chart represents less uncertainty in the prediction for that metric.

Figure 9:
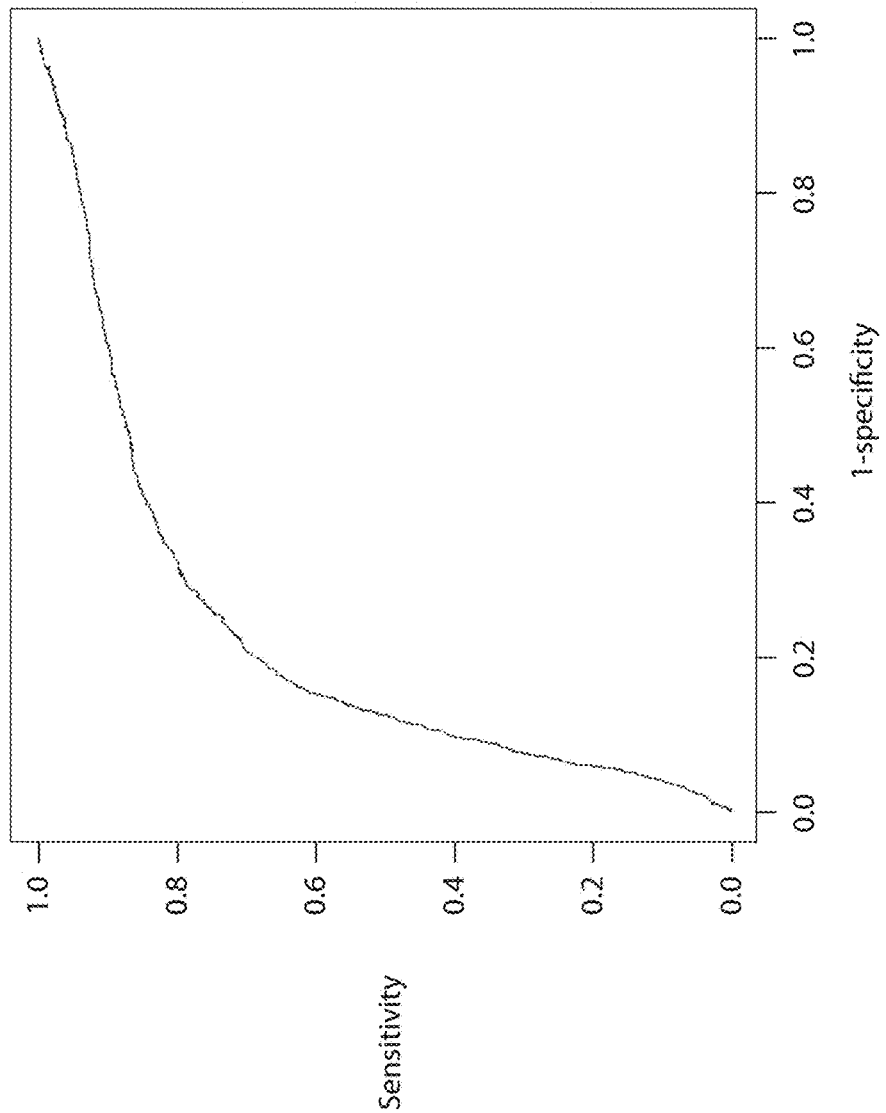
FIG. 9 is a Receiver Operator Curve ("ROC curve") built using classifiers according to methods of the invention.

As used herein "classifiers" are combinations of metrics in functions built using multivariate methods to increase the predictive ability of the method to distinguish melanoma from nevi. Classifiers may be obtained and optimized according to known techniques by maximizing the performance of a set of classifiers in receiver operator curve ("ROC") maximization. ROC maximization for classifiers distinguishing melanoma from nevi are reproduced in FIG. 9, which plots specificity (true negative rate) versus sensitivity (true positive rate), such that a maximum area under the curve in FIG. 9 represents an accurate classifier.

The output of a classifier is a percent likelihood that a lesion is melanoma, which may be coupled with a percent error or uncertainty for the classifier. This can be output for the user in any desired format. A dermatologist may want to see the underlying statistical information displayed as numbers and graphs, either on the device LCD screen, or on the screen of the computer communicating with the device. The ordinary patient may prefer an intuitive system of identifying potentially dangerous lesions, where the lesions most likely to be melanomas are identified with a red light and the least dangerous with a green light.

In order to develop the classifiers, a sample of nevi of known pathology was obtained and classifiers were developed using a "training" subset of the sample using both linear techniques (such as regressions and linear discriminant analysis) and nonlinear techniques (such as neural networks and decision tree algorithms). The following linear classifier is an example of a classifier developed from a training set having some predictive ability to discriminate between nevi and melanoma:

$$L=0.16*\text{range}-0.87*\text{edge}+0.68$$

where range and edge are metrics defined above and L represents a classifier that may be compared to a threshold to yield a classification of melanoma or nevus. "Training" was possible because the pathology of the lesions was known from prior pathologist screening, and the metrics and constants may be selected to maximize the area under the ROC curve. Subsequently, the "trained" classifiers are applied to lesions having unknown pathology. (In the experimental setting this means that the investigator was blind to the pathology of the lesions and did not adjust the classifiers; in the real world setting the device will typically be applied only to lesions having unknown pathology, and the thresholds and classifiers will be pre-programmed) As would be apparent to one of ordinary skill in the art, a larger training sample and slight variation of the metrics will likely yield improved classifiers, without departing from the scope of the invention. Once obtained, the classifiers are applied to the image data of lesions whose pathology is unknown. According to the invention, a selectivity/specificity of 86%/91% was obtained, with an overall diagnostic accuracy of 89%. This result is expected to improve with routine optimization.

The computer program reproduced in Table 2 describes and enables in detail the data processing steps described herein.

TABLE 2

```
% Daniel Gareau 2013
% This code loads a set of images and prompts the user to crop them
% create a folder in the same parent folder of this code and put the
% images in there that you want to analyze
    clear all
    close all
User inputs
    crop = 1; % Binary choice of "crop mole from orig img"
    clearbord = 1;
read data
    cd FolderName % change this to the name of the folder that contains images
    %dirnames = dir('*.bmp'); % enable this line if they are bitmaps
    dirnames = dir('*.jpg');    % enable this line if they are jpegs
    %dirnames = dir('*.tif');   % enable this line if they are TIFFs
    Nims = length(dirnames);
    for i = 1:length(dirnames)
        name_i = dirnames(i,:).name;
        %datt = imread(name_i,'bmp'); % enable this line if they are bitmaps
        datt = imread(name_i,'jpg');    % enable this line if they are jpegs
        %datt = imread(name_i,'tif');   % enable this line if they are TIFFs
        datt0 = datt;
        [Ny Nx Nz] = size(datt);
        sizelist = sort([Nx Ny]);
plot
        figure(1)
        subplot(3,2,1)
        imshow(datt)
        title('Original Image','fontsize',16)
        axis off
        axis image equal
isolate blue channel of jpg
        slice = zeros(Ny,Nx);
        slice = datt(:,:,3);%/var*256;
User crop
        if crop
            figure(88)
            imagesc(datt)
            drawnow
            title('click top left and bottom right within the lesion');
            cc = ginput;
            xmin = ceil(cc(1,1));
            xmax = ceil(cc(2,1));
            ymin = ceil(cc(1,2));
            ymax = ceil(cc(2,2));
            window = [ xmin xmax ymin ymax ];
            slice(:,window(2):Nx) = [ ];
            slice(:,1:window(1)) = [ ];
            slice(window(4):Ny,:) = [ ];
            slice(1:window(3),:) = [ ];
            RR = zeros(Ny,Nx);
            RR = datt(:,:,1);
            GG = zeros(Ny,Nx);
            GG = datt(:,:,2);
            RR(:,window(2):Nx) = [ ];
            RR(:,1:window(1)) = [ ];
            RR(window(4):Ny,:) = [ ];
            RR(1:window(3),:) = [ ];
            GG(:,window(2):Nx) = [ ];
            GG(:,1:window(1)) = [ ];
            GG(window(4):Ny,:) = [ ];
            GG(1:window(3),:) = [ ];
            datt_marked = zeros(ymax-ymin-1,xmax-xmin-1,3);
            datt_marked(:,:,1) = RR;
            datt_marked(:,:,2) = GG;
            datt_marked(:,:,3) = slice;
            clear datt
            datt = datt_marked;
        end
Save Struct
        Out(i).name = name_i;
        Out(i).cropPOS = cc;
```

TABLE 2-continued

```
            Out(i).OrigImg = datt0;
            Out(i).CropImg = datt;
    End
    save Pre_Processed Out
    cd ..
    % Daniel Gareau 2013
    % Works for RGB or N-layer image
    clear all
    close all
    Nvars = 17; % number of output metrics to describe malignancy
    Nlayers = 3;% number of color layers, 3 for RGB but could be more
    Nims = 240; % the number of images in the data set
    Matrix_Out = zeros(Nlayers,Nims,Nvars);
    homeDIR = pwd;                          % Define Home Directory
    global RADlength THESIZE i_Asym_Keep i_layer slice dat4MATH datt mole plotON
    Set_Up_Figures                 % sets up figures
    %warning off
User inputs
    cd Sarah1-2-3 % Change Directory to folder where data lies
    clearbord = 1;   % if clearbord = 1, don't count moles that touch image border
    n_ang = 18;                       % analyze flip symmetry over 180 degrees
    d_ang = 10;                       % in 10 degree incriments
    ThreshMelNetw = 0.7;              % The higher this number, the less restrictive in determining
Plotting choices
    plotON_Thresh = 0;                 % shows thresholding
    plotON_GetStats =1;                % shows edge fitting
    plotON_Sym = 0;                    % shows symmetry flipping boarder rotation routine
    plot_pix_dist = 0;                 % shows pixel distribution for threshold finder
    plotON_ShowCentroid = 0;
    plotON_Topo = 0;                   % Shows topographical map based on spectrum
    plot_CoordXfer = 1;                % shows coordinate transformation
Debugging tools
    use_whole = 1;              % Use entire image for automatic thresholding
    debugR = 0;                 % debug the red channel image segmentation
    debug_it = 1;
    hold_it = 0;   % if this = 1, do not ask for input positions
    %getvals = 1;
    FilterOutSlopes = 1;
    options = optimset('Display','off', 'MaxIter',200);
Set wavelength Information for Data Spec.
    LayerNames = [ % this is the whole spectral image cube, could be N wavelengths
            'R'
            'G'
            'B'];
    Lambda = [ % these are the peak wavelengths of the spectral images in [nm]
            633
            532
            488];
    Color_Order = [ 1 2 3 ]; % Pick display "R" "G" "B" wavelength data to DISPLAY % data
    clr = 'rgb';
load Data
            targetDIR = pwd;
            load Pre_Processed
            Nims = length(Out);
            Results_cache = zeros(Nims,40); %
            try
            load UsrCash
            catch
            end
            cd ..
CRUNCH THFE DATA
THESIZE = 200; % N Bins for both number of radii in half circle and number of pixels
just_starting = 0; % flag to Initialise Output Matrix
for i = Nims-12 % 127 % 235%
            disp(sprintf('Now working on Mole %3.0f of %3.0f', i, Nims));
            datt = Out(i).CropImg;
            [Ny, Nx, Nlayers] = size(datt);
            Xkeep1 = zeros(Nlayers,1);
            Xkeep2 = Xkeep1;
            Ykeep1 = Xkeep1;
            Ykeep2 = Xkeep1;
            sz = mean([Ny Nx]);
MinMol = round((sz/6)^2); % the min size of the mole should be a quarter of
                        % the lateral field of view
dat4MATH = Out(i).CropImg;
dat4SHOW = zeros(size(dat4MATH));
dat4SHOW(:,:,1) = dat4MATH(:,:,Color_Order(1));
dat4SHOW(:,:,2) = dat4MATH(:,:,Color_Order(2));
dat4SHOW(:,:,3) = dat4MATH(:,:,Color_Order(3));
figure(1);clf
```

TABLE 2-continued

```
subplot(3,3,1)
imagesc(dat4SHOW(:,:,1)/256, [0 1])
hold on
title(sprintf([LayerNames(1) ' - ' num2str(Lambda(1))]),'fontsize',14)
axis off
axis image
colormap gray
subplot(3,3,2)
imagesc(dat4SHOW(:,:,2)/256, [0 1])
hold on
title(sprintf([LayerNames(2) ' - ' num2str(Lambda(2))]),'fontsize',14)
axis off
axis image
colormap gray
subplot(3,3,3)
imagesc(dat4SHOW(:,:,3), [0 256])
hold on
title(sprintf([LayerNames(3) ' - ' num2str(Lambda(3))]),'fontsize',14)
axis off
axis image
colormap gray
%colorbar
subplot(3,3,4)
imagesc(datt/256)
hold on
title(sprintf([Out(i).name]),'fontsize',14)
axis off
axis image
drawnow
subplot(3,3,5)
imagesc(datt/256)
hold on
title(sprintf([Out(i).name]),'fontsize',14)
axis off
axis image
drawnow
RADlengths = zeros (2*THESIZE+1,Nlayers);
%Xkeep2 = zeros(Nlayers);
%Ykeep1 = zeros(Nlayers);
MoleArea = zeros(Nlayers,1);
i_Asym_Keep = zeros(Nlayers,1);
go through the images at different wavelengths
        for i_layer = 1:Nlayers
                % for instance an RGB image would have Nlayers = 3
                %try
isolate chromatic channel images of multispec- tral image cube
                slice = datt(:,:,i_layer);
                slice0 = slice;
                if use_whole == 1; % use whole image to determine lesion threshold
                        xx1 = 1;
                        yy1 = 1;
                        xx2 = Nx;
                        yy2 = Ny;
                else
                        ManualThresh
                end
                n4hist = 100;
                samp=slice(yy1:yy2,xx1:xx2)
                ;
                samp= reshape(samp,(yy2-yy1+1)*(xx2-xx1+1),1);
                mmm= mean(samp);
                [hist_n, hist_val] =
                hist(samp,n4hist); [hist_n]=
                smooth(hist_n,10);
                TTT = mmm;
Thresholding by Otsu's method
                for i_iterate = 1:10   % Implement Otsu's thresholding
                        method i_low = 0;
                        LowSide = 0;
                        i_high = 0;
                        HighSide = 0;
                        for iloop =
                    1:length(samp) if
                    samp(iloop) < TTT
                                i_low = i_low + 1;
                                LowSide = LowSide + samp(iloop);
                        end
                        if samp(iloop) > TTT
                                i_high = i_high +
                                1;
```

TABLE 2-continued

```
                            HighSide = HighSide + samp(iloop);
                    end
                end
                TTT = (HighSide/i_high + LowSide/i_low)/2;
end
if plot_pix_dist == 1
                if i_layer == 1
                    figure(5);clf
                else
                    figure(5)
                end
                plot(hist_val,hist_n, [clr(i_layer) '-'],'linewidth',2)
                hold on
                plot(TTT,0,[clr(i_layer) 'o'],'markerfacecolor',clr(i_layer))
                xlabel('pixel brightness','fontsize',16)
                ylabel('number of pixels','fontsize',16)
                title('thresholding pixel histogram','fontsize',16)
                set(gca,'fontsize',16)
end
mole=1-
im2bw(slice/max(max(max(slice))),TTT/max(max(max(slice))));
if debugR == 1
                figure(69)
                subplot(2,2,1)
                imagesc(moleR/256)
                colorbar
                stop
end
if
                plotON_Thresh
                figure(2);
                clf
                subplot(3,
                3,1)
                imagesc(slice) axis
                image
                title('Original
                Image') axis off
                colormap
                gray
                subplot(3,
                3,2)
                imagesc(mole) axis
                image
                title('Threshold
                Applied') axis off
                colormap gray
end
seD = strel('diamond',1);
mole = bwareaopen(mole,MinMol);
if
                plotON_Thresh
                subplot(3,
                3,3)
                imagesc(mole) axis
                image
                title('bwareaopen') axis off
                colormap gray
end
mole = imfill(mole,'holes');
if plotON_Thresh
                subplot(3,3,4)
                imagesc(mole)
                axis image
                title('imfill')
                axis off
                colormap gray
end
mole = imerode(mole,seD);
if plotON_Thresh
                subplot(3,3,5)
                imagesc(mole)
                axis image
                title('imerode')
```

TABLE 2-continued

```
                            axis off
                            colormap gray
                    end
                    masked = mole.*slice;
                    if plotON_Thresh
                            subplot(3,3,6)
                            imagesc(masked)
                            axis image
                            title('masked')
                            axis off
                            colormap gray
                    end
                    if clearbord
                            mole = imclearborder(mole,4);
                            masked = mole.*slice;
                            if plotON_Thresh
                        subplot(3,3,6)
                        imagesc(masked)
                        axis image
                        title('masked')
                        axis off
                        colormap gray
                            end
                    end
                    mole = bwareaopen(mole,MinMol);
                    if i_layer == 1
                            Topo = mole;
                    else
                            Topo = Topo + mole;
                    end
                    Outline = bwperim(mole,8);
                    slice0(Outline) = 255;
                    fracDIM = Fractal2(mole);
                    [B, L] = bwboundaries(mole,'nohole');
                    stats = regionprops(L,'all');
                    stringdat = double(reshape(slice,Nx*Ny,1));
                    var = mean(stringdat)+3*std(stringdat);
                if plotON_Thresh
                            subplot(3,3,7)
                            imagesc(mole)
                            axis image
                            title('bwareaopen2')
                            axis off
                            colormap gray
                            subplot(3,3,8)
                            imagesc(Outline)
                            axis image
                            title('Outline')
                            axis off
                            colormap gray
                            subplot(3,3,9)
                            imagesc(slice0)
                            axis image
                            title('Marked')
                            axis off
                            colormap gray
                    end
analyze lesion segment pixels
                    PixList = stats.PixelList;
                    nn = length(PixList);
                    sampled = zeros(nn,1);
                    for ii = 1:nn
                            sampled(ii) = slice0(PixList(ii,2),PixList(ii,1));
                    end
                    colorVAR = std(sampled)/mean(sampled);
analyze symmetry
                    X = round(stats.Centroid(1));
                    Y = round(stats.Centroid(2));
    %               Xkeep2(i_layer) = 0;
    %               Ykeep1(i_layer) = 0;
                    Just_Mole = masked.*mole;
                    if plotON_ShowCentroid
                            figure(8);clf
                            subplot(2,2,1)
                            imagesc(Just_Mole)
                            axis image equal
                            axis off
                            colormap gray
                            colorbar
                            title('original')
```

TABLE 2-continued

```
                end
        BWw = Just_Mole > 0 ;
        minJM = min(min(Just_Mole));
        %maxJM = max(max(Just_Mole));
        Just_Mole = Just_Mole − minJM;
        Just_Mole = Just_Mole.*mole;
        if plotON_ShowCentroid
                        figure(8)
                        subplot(2,2,2)
                        imagesc(Just_Mole)
                        axis image equal
                        axis off
                        colormap gray
                        colorbar
                        title('zeroed out')
        end
        Just_Mole = Just_Mole/max(max(Just_Mole)); % Normalize
        if plotON_ShowCentroid
                        figure(8)
                        subplot(2,2,3)
                        imagesc(Just_Mole)
                        axis image equal
                        axis off
                        colormap gray
                        colorbar
                        title('Normalised')
        end
        Just_Mole = 1−Just_Mole; % Invert
        Just_Mole = Just_Mole.*mole;
        if plotON_ShowCentroid
                        figure(8)
                        subplot(2,2,4)
                        imagesc(Just_Mole)
                        hold on
                        axis image equal
                        axis off
                        colormap gray
                        colorbar
                        title('Inverted')
        end
        MelNetFlag = −1;
        if i_layer == Nlayers
                        clear BW
                        BW = Just_Mole;
                        %FindCorrDecay % -->
                        %TestMelNetwork = factor_catch;
                        %MelNetFlag = 0;
              % if TestMelNetwork < ThreshMelNetw
                        %   MelNetFlag = 1;
                        %end
        end
%
%           figure(56)
%           subplot(2,1,1)
%           imagesc(masked.*mole)
%           %BWw > 0 = 256−(BWw > 0)
        statsWeighted = regionprops(BWw, Just_Mole, ...
                {'Centroid','WeightedCentroid'});
        tempCTR = statsWeighted.WeightedCentroid;
        Xw = round(tempCTR(1));
        Yw = round(tempCTR(2));
        if plotON_ShowCentroid
                        figure(8)
                        subplot(2,2,4)
                        plot(Xw,Yw,[clr(i_layer) '*'])
        end
        Xkeep1(i_layer) = X;
        Ykeep1(i_layer) = Y;
        Xkeep2(i_layer) = Xw;
        Ykeep2(i_layer) = Yw;
        sizelist2 = sort([Xw Yw]);
        nnn = sizelist2(1)−1;
        brd = stats(1).Perimeter/sqrt(stats(1).Area) − 2*pi/sqrt(pi);
        clear dif dif2 Assym2
        XXX = zeros(n_ang,1); % initialize arrays
        YYY = XXX;
        Assym2 = XXX;
        for ii = 1:n_ang
                        deg_rot = ii*d_ang;
                        clear B L rotated ctr stats.Centroid flipout2 dif2
```

TABLE 2-continued

```
            rotated = logical(imrotate(mole,deg_rot,'nearest','loose'));
            [Ny, Nx] = size(rotated);
            rotated = bwareaopen(rotated,MinMol);
            [B, L] = bwboundaries(rotated,'nohole');
            stats2 = regionprops(L,'all');
            XX = round(stats2.Centroid(1));
            YY = round(stats2.Centroid(2));
            XXX(ii) = XX;
            YYY(ii) = YY;
            flipout2 = rotated';
            [BB, LL] = bwboundaries(flipout2,'nohole');
            stats3 = regionprops(L,'all');
            XXf = round(stats3.Centroid(1));
            YYf = round(stats3.Centroid(2));
            sizelist2 = sort([XX YY]);
            nnn = sizelist2(1)-1;
            factorBIG = 4;
            dif2 = zeros(factorBIG*nnn,factorBIG*nnn);
            for iii = 1:factorBIG*nnn
          for j = 1:factorBIG*nnn
                 if YY-XXf+iii > 0 && XX-YYf+j > 0 && XX-YYf+j < Nx ...
                      && YY-XXf+iii < Ny && j < Ny && iii < Nx
                     dif2(j,iii) = abs(rotated(j,iii) - ...
                           flipout2(XX-YYf+j,YY-XXf+iii));
                  end
           end
            end
            [NdiffY, NdiffX] = size(dif2);
            Assym2(ii) = sum(reshape(dif2,NdiffX*NdiffY,1))/nn;
            if plotON_Sym == 1
         if ii == 1
                  figure(3)
                  clf
            end
            figure(3)
            subplot(3,6,ii)
            imagesc(dif2)
            hold on
            %axis([XX-nnn XX+nnn YY-nnn YY+nnn])
            axis equal
            axis off
            axis([XX-nnn XX+nnn YY-nnn YY+nnn])
            colormap gray
            title(sprintf('A = %0.4f',Assym2(ii)))
            plot(XX,YY,'gx')
                  end
end
[Big_Asym, garbage] = max(Assym2);
[sym, i_sym] = min(Assym2);
if i_sym == 9
            i_sym = 8;
end
if i_sym == 18
            i_sym = 17;
end
if plotON_Sym == 1
            subplot(3,6,i_sym)
            plot(XXX(i_sym),YYY(i_sym),'bo','markerfacecolor','b')
end
n_shift = round(90/d_ang);
i_Asym = i_sym +
n_shift; if i_sym >
n_ang/2
            i_Asym = i_sym - n_shift;
end
Asym(i) =
Assym2(i_Asym); if
plotON_Sym == 1
            subplot(3,6,i_Asym)
            plot(XXX(i_Asym),YYY(i_Asym),'ro','markerfacecolor','r')
end
i_Asym_Keep(i_layer) =
i_Asym; [Nxx, Nyy] =
size(slice); ThetaTS =
(i_sym*d_ang)*pi/180;
ThetaTS_asym = (i_Asym*d_ang)*pi/180;
for ix = 1:X
            xplot =
            X+ix;
            xplotN =
```

TABLE 2-continued

```
                        X-ix;
                        yp = Y-
                        ix*tan(ThetaTS); yn =
                        Y+ix*tan(ThetaTS);
                        yyp = Y-
                        ix*tan(ThetaTS_asym); yyn =
                        Y+ix*tan(ThetaTS_asym);
                        if round(xplot) > 0 && round(xplot) < Nyy && round(yp) > 0
                            . . . && round(yp) < Nxx
                    if     mole(round(yp),round(xp
                                lot)) x1 = xplot;
                                y1 = yp;
                        end
                          end
                        if round(xplotN) > 0 && round(xplotN) < Nyy && round(yn) > 0
                    ... && round(yn) < Nxx
                    if
                                mole(round(yn),round(xpl
                                otN)) x2 = xplotN;
                            y2 = yn;
                        end
                          end
                        if round(xplot) > 0 && round(xplot) < Nyy && round(yyp) > 0
                            ... && round(yyp) < Nxx
                    if
                                mole(round(yyp),round(xp
                                lot)) x1_asym = xplot;
                                y1_asym = yyp;
                        end
                          end
                        if round(xplotN) > 0 && round(xplotN) < Nyy && round(yyn) > 0
                    ... && round(yyn) < Nxx
                    if
                                mole(round(yyn),round(xpl
                                otN)) x2_asym = xplotN;
                                y2_asym =
                                    yyn;
                        end
                          end
            end
            diampix1 = sqrt((x1_asym-x2_asym)^2+(y1_asym-y2_asym)^2);
            diampix2 = sqrt((x1-x2)^2+(y1-y2)^2);
            diampix = (diampix1 + diampix2)/2;
            getSTATS % do the clock sweep analysis
            range_mean = (max(RADmean) - min(RADmean))/mean(RADmean);
            std_mean = std (RADmean)/mean(RADmean);
            range_std = mean(RADstd);
            std_std = std(RADstd);
            dth = 360/length(RADmean);
            theta_plot = (1:length(RADmean))*dth;
            figure(1)
            subplot(3,3,6)
            plot (theta_plot,RADmean,[clr(i_layer) '-'],'linewidth',4)
            hold on
            text(0-5,0,'0')
            text(90-10,0,'\pi/2')
            text(180-5,0,'\pi')
            text(270-15,0,'3\pi/2')
            text(360-10,0,'2\pi') axis
            off
            title('Clock-Sweep Melanoma Radar') hold on
            SmoothRad = smooth(RADmean,8);
            for isamp = 1:length(RADmean)
                        plot([isamp isamp]*dth,[SmoothRad(isamp)-RADstd(isamp) ...
                        SmoothRad(isamp)+RADstd(isamp)],'k-') hold on
            end
            axis([0 360 0 200])
            ylabel('brightness')
            plot(theta_plot,SmoothRad, [clr(i_layer) '-
            '],'linewidth',2)
calculate the first order derivitave numerically
            RADdir = zeros( length(theta_plot),1 ); for
            isamp = 1:length(RADmean)-1
                        RADdir(isamp) = abs(SmoothRad(isamp)-SmoothRad(isamp+1));
            end
            RADdir(length(SmoothRad)) = abs(SmoothRad(length(SmoothRad))- ...
                        SmoothRad(1)); % Loop around!
Condition the function to specify the shoulder edge sharpness
            Out_slope = Out_slope/sqrt(stats.Area);
            % this normalizes the edge thickness to the lesion size
```

TABLE 2-continued

```
goodOUT = goodOUT/sqrt(stats.Area);
% this normalises the edge thickness to the lesion size
figure(1)
subplot(3,3,9)
tempTHplot = (1:length(Assym2))./length(Assym2)*360;
plot(tempTHplot,Assym2*50,'kx','markersize', 8)
hold on
plot(tempTHplot(i_Asym),Assym2(i_Asym)*50,'ro',...
        'markerfacecolor','r')
plot(tempTHplot(i_sym),Assym2(i_sym)*50,'bo', ...
        'markerfacecolor','b')
Steve_U = (2:length(theta_plot)-2);
plot(theta_plot(Steve_U), RADdir(Steve_U)*10, ...
        [clr(i_layer) '-'], 'linewidth', 2) plot(theta_plot,100-
Out_slope*70, [clr(i_layer) '-'], ...
        'linewidth', 2) % / number of pixels in lesion mole
%legend('shoulder', 'hot spots', 'demarcation')
text(0-5,-5,'0')
text(90-10,-5,'\pi/2')
text(180-5,-5,'\pi')
text(270-15,-5,'3\pi/2')
text(360-10,-5,'2\pi')
axis([0 360 0 100])
axis off
mean_OutSlope = mean(goodOUT');
std_OutSlope = std(goodOUT);
nametemp = Out(i).name;
JustNum = str2double(nametemp(2:5));
%           if just_starting = 0   % Initialize Output Matrix
%                   just_starting = 1;
%                   Nvars = 17;
%                   Matrix_Out = zeros(Nlayers,Nims,Nvars);
%           end
if i_layer == 3
Mel_score = 4.434832*range_mean - 24.74571*std_mean - ...
        0.014718*range_std + 0.115176*std_std - 2.8412*mean(RADdir(Steve_U)) ...
        -0.699533*std(RADdir(Steve_U)) - 0.007139*sum(RADdir(Steve_U)) ...
        + 2.322288*Big_Asym/stats.Eccentricity ...
        +0.753011*Asym(i) + 0.094436*brd + 19.046680*mean_OutSlope + ...
        12.46769*std_OutSlope + 0.195133*fracDIM...
        -0.040476*colorVAR - 0.001002*mean(Out_flagVAL(:,2)) + ...
        0.000828*std(Out_flagVAL(:,2));
figure(1)
subplot(3,3,5)
title(sprintf('DanScore = %3.3f',Mel_score));
end
            Matrix_Out(i_layer,i,1) = JustNum; Matrix_Out(i_layer,i,2) =
            range_mean; % F(lambda)
            Matrix_Out(i_layer,i,3) = std_mean; % F(lambda)
            Matrix_Out(i_layer,i,4) = range_std; % F(lambda)
            Matrix_Out(i_layer,i,5) = std_std; % F(lambda)
            Matrix_Out(i_layer,i,6) = mean(RADdir(Steve_U)); % F(lambda)
            Matrix_Out(i_layer,i,7) = std(RADdir(Steve_U)); % F(lambda)
            Matrix_Out(i_layer,i,8) = sum(RADdir(Steve_U)); % sum of hotspots (change
            Matrix_Out(i_layer,i,9) = Big_Asym/stats.Eccentricity; % F(lambda)
            Matrix_Out(i_layer,i,10) = Asym(i); % F(lambda)
            Matrix_Out(i_layer,i,11) = brd; % F(lambda)
            Matrix_Out(i_layer,i,12) = mean_OutSlope; % F(lambda)
            Matrix_Out(i_layer,i,13) = std_OutSlope; % F(lambda)
            Matrix_Out(i_layer,i,14) = fracDIM; % F(lambda)
            Matrix_Out(i_layer,i,15) = colorVAR; % F(lambda)
            Matrix_Out(i_layer,i,16) = mean(Out_flagVAL(:,2)); % F(lambda)
            Matrix_Out(i_layer,i,17) = std(Out_flagVAL(:,2));
                        % NOTE!!! Must update the number of output metrics just above!
            figure(1)
%             subplot(3,3,4)
%             lesion_ctr = round;stats.Centroid);
%             plot(lesion_ctr(2),lesion_ctr(1),[clr(i_layer) '*'])
            MoleArea(i_layer) = stats.Area;
subplot(3,3,5)
imagesc(datt/256)
hold on
%title(sprintf([Out(i).name]),'fontsize',14)
axis equal image
axis off
dummyIM = ones(150,1000,3);
subplot(3,3,7)
imagesc(dummyIM)
axis off
text(5,0-40,sprintf('%3.3f = ang. brightness range',range_mean))
```

TABLE 2-continued

```
                    text(5,15-40,sprintf('%3.3f = ang. brightness var.',std_mean))
                    text(5,30-40,sprintf('%3.3f = ave. var. over radials',range_std))
                    text(5,46-40,sprintf('%3.3f = var. of var. over radials',std_std))
                    text(5,60-40,sprintf('%3.3f = derivitave avg. over sweep', ...
                            mean(RADdir(Steve_U))))
                    text(5,75-40,sprintf('%3.3f = derivitave var. over sweep', ...
                            std(RADdir(Steve_U))))
                    text(5,90-40,sprintf('%3.3f = sum HotSpots',sum(RADdir(Steve_U))))
                    text(5,105-40,sprintf('%3.3f = assysmetry (computer)', ...
                            Big_Asym/stats.Eccentricity))
                    text(5,120-40,sprintf('%3.3f = assymetry (clinical)',Asym(i)))
                    text(5,135-40,sprintf('%3.3f = border roughness',brd))
                    text(5,150-40,sprintf('%3.3f = edge sharpness',mean_OutSlope))
                    text(5,165-40,sprintf('%3.3f = var. of edge sharpness' ...
                            ,std_OutSlope))
                    text(5,180-40,sprintf('%3.3f = Fractal Dimension',fracDIM))
                    text(5,195-40,sprintf('%3.3f = ColorVariation',colorVAR))
                    text(5,210-40,sprintf('%3.3f = Mean Edge Fit err', ...
                            mean(Out_flagVAL(:,2))))
                    text(5,225-40,sprintf('%3.3f = Std Edge Fit Error', ...
                            std(Out_flagVAL(:,2))))
                    text(5,240-40,sprintf('%1.0f = Mel. Network Found',MelNetFlag))
                    RADlengths(:,i_layer) = RADlength;
%                   catch % for try up at the beginning
%                       end
            end
            if Nlayers == 3
                    %Blue_Flag = 0
                    makeCOLORimg;
                    figure(6);clf
                    subplot(2,2,1);
                    %COLORimg_prnt = flipdim(COLORimg,1);
                    %COLORimg_prnt = flipdim(COLORimg_prnt,2);
                    %imagesc(flipdim(COLORimg,1)/max(max(max(COLORimg))));
                    imagesc(COLORimg/max(max(max(COLORimg))));
                    axis equal image
                    axis off
                    i_colors = 0;
                    sums_color = sum(sum(ColorMaps));
                    for i_check_colors = 1:length(Colors)
                            if sums_color(i_check_colors)
                                i_colors = i_colors + 1;
                            end
                    end
                    title(sprintf('%1.0f colors found',i_colors));
                    if plotON_Topo
                            H = fspecial('average', [10 10]);
                            Topo_sm = imfilter(-Topo, H);
                            X_surf = 1:Nx;
                            Y_surf = 1:Ny;
                            Z_surf = -1:min(min(Topo));
                            figure(10);clf
                            %TopoSurf = meshgrid(Topo);
                            %surf(X_surf,Y_surf,Z_surf,Topo_sm)
                            surf(Topo_sm.*(Topo>0))
                            %axis vis3D
                            %zlim([min(min(Topo_sm)) -0.5])
                            %colormap gray
                    end
                    %Find_Vessles
            end
        Assign_Results
            % initializes all Total Output Results to -1
            % then assigns current val if possible
            eval(['cd ' targetDIR])
            cd ResultsImages
            name = sprintf(['Out',Out(i).name]);
            print(figure(1),'-djpeg','-r600',name);
            name2 = sprintf(['OutClr',Out(i).name]);
            print(figure(6),'-djpeg','-r600',name2);
            eval(['cd ' homeDIR])
    end
    write results
        eval(['cd ' targetDIR])
        xlswrite('TOTAL_AutoSavedResult',total_AutoSavedResult)
        if use_whole == 0
                save UsrCash Results_cache
                xlswrite('AutoSaveResult',Results_cache)
        end
        save Matrix_Result Matrix_Out                       total_AutoSavedResult
```

TABLE 2-continued

```
eval(['cd ' homeDIR])
makeXLSspreadsheets
%
% figure(97)
% plot(SmoothRad,'b-', 'linewidth',2)
% axis([0 length(SmoothRad) 0 1.2*max(SmoothRad)])
% Daniel Gareau 2013
function err = fitERF(start)
global dummy plot_on THESIZE
%i_middle = start(1);
bbb = start(1);
offRr = start(2);
Cmax = start(3);
xxtemp = [1:length(dummy)];
ppp_erf1 = erf((xxtemp - round(THESIZE/2))/bbb);
ppp_erf = offRr + (ppp_erf1/2 - min(ppp_erf1/2))*Cmax;
err = sum(abs(sqrt(ppp_erf-dummy).^2 ));
if plot_on
        figure(65);clf
        plot(xxtemp,dummy,'k*')
        hold on
        plot(xxtemp,ppp_erf,'b-')
%   plot(xxtemp,ppp_erf1,'r-')
%   plot(xxtemp,ppp_erf2,'r--')
        drawnow
end
% Set_Up_Figures.m by Dan Gareau
% set(0,'Units','pixels') , then use get(figure(n),'position')
fignums = [1 2 3 4 5 6 7 8 9 10 ];
Posn = [
```

|      |    |     |     |     |     |
|------|----|-----|-----|-----|-----|
| 32   |    | 487 |     | 889 | 618 |
| 969  |    | 488 | 700 | 614 |     |
| 1944 |    | 678 |     | 530 | 20  |
| 33   | 54 | 254 | 333 |     |     |
| 305  | 56 | 319 | 332 |     |     |
| 646  | 58 | 406 | 327 |     |     |
| 1079 |    | 50  |     | 621 | 338 |
| 1946 |    | 199 |     | 527 | 377 |
| 2492 |    | 202 |     | 531 | 372 |
| 2495 |    | 675 |     | 560 | 420 |

```
    ];
    set(0,'Units','pixels')
    for i = 1:length(fignums)
        set(figure(fignums(i)),'position',[Posn(i,:)])
    end
% makeXLSspreadsheets.m
global i_layer
eval(['cd ' targetDIR])
load Matrix_Result % Matrix_Out(Nlayers,Nims,Nvars)
[Nlayers Nims Nvars] = size(Matrix_Out);
clear Matrix_Write
Matrix_Write = zeros(Nims,Nvars);
for i_layer = 1:Nlayers
        Matrix_Write = shiftdim(Matrix_Out(i_layer,:,:),1);
        xlswrite(sprintf(['AutoSaveResult' num2str(i_layer)]),Matrix_Write)
end
eval(['cd ' homeDIR])
% makeCOLORimg.m
% Daniel Gareau 2013
global   FLAGS mole dat4MATH
sliceR = dat4MATH(:,:,1);
sliceG = dat4MATH(:,:,2);
sliceB = dat4MATH(:,:,3);
Colors = [ % wikipedia
```

| 40  | 26  | 13   | % dark-brown |
| 71  | 40  | 11   | % light-brown |
| 0   | 0   | 0    | % black |
| 100 | 0   | 0    | % red |
| 40  | 60  | 80   | % blue-gray |
| 100 | 100 | 100];| % white |

```
Colors = Colors/100*256;
Rm = [ % ratio mean    [r/b r/g b/g]    mean_rb_rg_bg
```

| 1.9006  | 2.0193 | 1.0656 | % dark-brown |
| 1.7247  | 1.6208 | 0.9431 | % light brown |
| 0.4648  | 0.7536 | 1.7404 | % black |
| 1.8058  | 1.9820 | 1.1040 | % red |
| %0.8286 | 1.0834 | 1.3094 | % blue-gray |
| 1.2598  | 1.3210 | 1.0515 | |
| %1.2649 | 1.2254 | 0.9768 | % blue-gray |
| 0.9243  | 1.2008 | 1.2998 | % white |

TABLE 2-continued

```
];
Rs = 3*[  % std
0.1429              0.1344       0.0721       % dark brown
0.1521              0.0877       0.0479       % light brown
0.1841              0.2127       0.3964       % black
0.2301              0.2032       0.0939       % red
%0.0702             0.0780       0.0464       % blue-gray
0.1143              0.0829       0.0436
%0.0666             0.0440       0.0253       % blue-gray
0.0342              0.0294       0.0257       % white
];
Rs(1,:) = Rs(1,:)*8;
Rs(2,:) = Rs(2,:)*3;
Rs(4,:) = Rs(4,:)/2;
%Rs(5,:) = Rs(5,:);
Rs(6,:) = Rs(6,:)*2;
COLORimg = zeros (Ny,nx,3)+256; % make solid color "painting"
%COLORimg(:,:,2) = 256; % make area outside of lesion seem green
ColorMaps = zeros(Ny,nx,length(Rs));
% max(max(slice))
%  min(min(slice))
FLAGS = zeros(6,1);
BlueFlag = −1;
for indexY = 1:Ny                          % scan image in y
    for indexX = 1:Nx                      % scan image in x
        % ratio of red to blue
        r_b = sliceR(indexY, indexX)/sliceB(indexY, indexX);
        r_g = sliceR(indexY,indexX)/sliceG(indexY,indexX);
        b_g = sliceB(indexY,indexX)/sliceG(indexY,indexX);
        for indexZ = 1:length(Rs)
                    % test to see if current pixel is each of 6 colors
                        % indexing: Rm(indexZ,2) indexZ−>row (putatuve color)
                        % 2−> pixeld ratio (r/g)
                        if    r_g <= Rm(indexZ,2)+Rs(indexZ,2) && ...
                              r_g >= Rm(indexZ,2)−Rs(indexZ, 2) ...
                        && r_b <= Rm(indexZ,1)+Rs(indexZ,1) && ...
                        r_b >= Rm(indexZ,1)−Rs(indexZ,1) ...
                        && b_g <= Rm(indexZ,3)+Rs(indexZ,3) && ...
                        b_g >= Rm(indexZ,3)−Rs(indexZ,3)
                          if mole(indexY,indexX) % if pixel is inside lesion
                              ColorMaps(indexY,indexX,indexZ) = 1;
                              COLORimg(indexY,indexX,1) = Colors(indexZ,1);
                              COLORimg(indexY,indexX,2) = Colors(indexZ,2);
                              COLORimg(indexY,indexX,3) = Colors(indexZ,3);
                              FLAGS(indexZ) = 1;
                          end
                        end
        end
    end
end
if sum(sum(ColorMaps(:,:,5))) > 20 | sum(sum(ColorMaps(:,:,6))) > 20
    BlueFlag = 1;
else
    BlueFlag = 0;
end
% getSTATS.m
% Daniel Gareau 2013
global getvals RADlength THESIZE theta plotON_GetStats i_layer clr ...
    dummy plotON_GetStats mean_OutSlope std_OutSlope Out_slope Which_Half
initializations
i_CountRadials = 0; % initialize for forward and backward for loops below
%i_GoodSlopes = 0; % initialize for forward and backward for loops below
XXXX = zeros(THESIZE,1);
YYYY = XXXX;
XXXXX = XXXX;
YYYYY = XXXX;
sampy = XXXX;
dummy = XXXX;
RADmean = zeros(THESIZE,1);
RADstd = zeros(THESIZE,1);
Out_slope = zeros(THESIZE,1);
if plot_CoordXfer
    OutXfer = zeros(THESIZE,THESIZE);
        % this is the matrix for angular to cartesian transfer output
end
if getvals
    Out_flagVAL = zeros(THESIZE,2);
end
for theta = −pi+pi/THESIZE:pi/THESIZE:pi+pi/THESIZE
 i_CountRadials = i_CountRadials+1;
```

TABLE 2-continued

```
for ix = 1:2*X
        xplot = X − sin(theta)*ix;
        yp = Y + cos(theta)*ix;
        if round(xplot) > 0 && round(xplot) < Nyy && round(yp) > 0 ...
                    && round(yp) < Nxx
                    if mole(round(yp),round(xplot))
                x1 = xplot;
                y1 = yp;
                    end
        end
end
if plotON_GetStats == 1
        figure(1)
        subplot(3,3,4)
        plot(x1,y1, [clr(i_layer) '.'],'markersize',2)
        if i_CountRadials == 1
                    plot(X,Y,[clr(i_layer) '*'])
                    plot(Xw,Yw,[clr(i_layer) 'o'])
        end
        drawnow
end
delX = x1−X;
delY = y1−Y;
XXXX = round((X:((delX)/THESIZE):x1)); % for pixels in lesion
YYYY = round((Y:((delY)/THESIZE):y1));
XXXXX = round((X+delX/2:(delX/THESIZE):X+delX*3/2)); % for edge
YYYYY = round((Y+delY/2:(delY/THESIZE):Y+delY*3/2));
if abs(delX) < 0.1 % if the radial is straight in x direction
        XXXX = zeros(length(YYYY),1);
        XXXX = XXXX + X;
        XXXXX = zeros(length(YYYYY),1);
        XXXXX = XXXXX + X;
end
if abs(delY) < 0.1 % if the radial is straight in x direction
        YYYY = zeros(length(XXXX),1);
        YYYY = YYYY + Y;
        YYYYY = zeros(length(XXXXX),1);
        YYYYY = YYYYY + Y;
end
rngY = max(YYYYY)−min(YYYYY);
rngX = max(XXXXX)−min(XXXXX);
norm_size = sqrt(rngY^2+rngX^2);
for i_samp = 1:THESIZE
            sampy(i_samp) = slice(YYYY(i_samp),XXXX(i_samp));
            if YYYYY(i_samp) > 0 && XXXXX(i_samp) > 0 && YYYYY(i_samp) < ...
                    Ny && XXXXX(i_samp) < Nx
                    dummy(i_samp) = slice(YYYYY(i_samp),XXXXX(i_samp));
            end
end
mid_dummy = min(dummy) + (max(dummy)−min(dummy))/2;
i_middle = 0;
for i_dmy = 1:length(dummy)
        if dummy(i_dmy) < mid_dummy % find 1/2max: initial fitting param
                    i_middle = i_dmy;
        end
        if dummy(i_dmy) < mid_dummy*1.5 % find 3/4max; initial fitting param
                    i_high = i_dmy;
                    end
end
if max(dummy) > 0
        delta_r = dummy(i_high) − dummy(i_middle);
        bbb = delta_r;
        offRr = min(dummy);
    Cmax = max(dummy);
    if dummy(round(length(dummy)/2)) > 0
                start = [bbb offRr Cmax];
                [resy, fval, exitflag, outMSG] = fminsearch('fitERF' ...
                        ,start,options);
                    if FilterOutSlopes
                            Out_flagVAL(i_CountRadials,1) = exitflag;
                            Out_flagVAL(i_CountRadials,2) = fval;
                    end
                    %resy = fminsearch('fitERF',start,options);
                    bbb = resy(1);
                    offRr = resy(2);
                    Cmax = resy(3);
                    Out_slope(i_CountRadials) = bbb/THESIZE*norm_size;
                    if plotON_GetStats == 1
                            figure(4)
                            subplot(2,1,2);
```

TABLE 2-continued

```
                        hold off
                        plot(dummy,'kx')
                        hold on
                        xxtemp = (1:length(dummy));
                        ppp_erf1 = erf(( xxtemp −round(THESIZE/2) )/bbb);
                        ppp_erf = offRr + (ppp_erf1/2 − min(ppp_erf1/2))*Cmax;
                        plot(ppp_erf,'k-','linewidth',2)
                        title(sprintf('lesion edge slope = %3.3f',bbb));
                        ylabel('Brightness');
                        xlabel('Pixels at the EDGE','fontsize',16);
                        axis([0 THESIZE min(dummy) max(dummy)])
                        drawnow
                    end
                end
            end
            if plotON_GetStats == 1
                    figure(4)
                    subplot(2,1,1)
                    hold off
                    plot (sampy,'k-','linewidth',2)
                    hold on
                    axis([0 THESIZE 0 256])
                    title('inside lesion')
                    ylabel('Brightness');
                    drawnow
            end
            RADmean(i_CountRadials) = mean(sampy);
            RADstd(i_CountRadials) = std(sampy);
            RADlength(i_CountRadials) = sqrt((x1−X)^2 + (y1−Y)^2);
            if plot_CoordXfer
                    OutXfer(i_CountRadials,:) = sampy;
                end
            end
            if FilterOutSlopes
                    i_good = 0;
                    %i_bad = 0;
                    for tttt = 1:length(Out_flagVAL)
                            if Out_flagVAL(tttt,1)
                                    i_good = i_good + 1;
                                    %Out_slope(i_CountRadials) = bbb/THESIZE*norm_size;
                                    goodOUT(i_good) = Out_slope(tttt);
                                    goodOUT_fval(i_good) = Out_flagVAL(tttt,2);
                            else
                                    Out_slope(tttt) = mode(Out_slope);
                                    %i_bad = i_bad + 1;
                                    %      badOUT(i_bad) = Out_slope(tttt);
                                    %      badOUT_fval(i_good) = Out_flagVAL(tttt,2);
                                    %Out_flagVAL(i_CountRadials,2) = fval;
                            end
                    end
            end
            if plot_CoordXfer
                    figure(65)
                    imagesc(OutXfer');
                    colormap gray
                    xlabel('Angle from zero to 360 degrees', 'fontsize',18)
                    ylabel('Radius from lesion center (top) to periphery (bottom)', ...
                        'fontsize',18)
                    title('Angular brightness map' , 'fontsize',18)
                    colorbar
                    figure(67)
                    imagesc(dat4SHOW(:,:,3))
                    colormap gray
                    axis off
                    %xlabel('Angle from zero to 360 degrees', 'fontsize',18)
                    %ylabel('Radius from lesion center (top) to periphery (bottom)', 'fontsize',18)
                    title('Original Image' , 'fontsize',18)
            end
end
Find_Vessels.m
                    By Dan Gareau 8/10/2013
                    % Vessels 143 156 187 210 176 235
Global dat4MATH i_ref name_4Joel_temp
Pickit = 0; % 1 to pick a new seed for region sampling
SeedFrac = 32; % multiplier to reduce threshold from fullscale (the higher
                    % SeedFrac)
FactorRED =1.5; % the higher FactorRED, the more vessels get selected
[Ny,Nx,Nz] = size(dat4MATH);
if Pickit
        figure(43);clf
        imagesc(dat4MATH/max(max(max(dat4MATH))))
```

TABLE 2-continued

```
                axis equal image
                axis off
                MARKED = dat4MATH/max(max(max(dat4MATH)));
                [b,a] = ginput;
                x = round(a);
                y = round(b);
                t = dat4MATH(y,x,2)/SeedFrac;
                J = regiongrowing(dat4MATH(:,:,2),x,y,t);
                %cd Saved
                %save MaskJ J x y SeedFrac
        else
                %load MaskJ % --> J
                redlevels = dat4MATH(:,:,1).^2./(dat4MATH(:,:,2) + dat4MATH(:,:,3));
                redlevels = redlevels.*mole;
                [junk resMAXy] = max(max(redlevels,[ ],1));
                [junk resMAXx] = max(max(redlevels,[ ],2));
                xt = round(resMAXx);
                yt = round(resMAXy);
% figure(1)
% subplot(3,3,4)
% plot(xt,yt,'kx')
                t = dat4MATH(xt,yt,2)/SeedFrac;
                J = regiongrowing(dat4MATH(:,:,2),xt,yt,t);
        end
% figure(7)
% subplot(3,3,10)
% imagesc(dat4MATH/max(max(max(dat4MATH))))
% axis equal image
% axis off
% title(name_4Joel_temp)
itt = 0;
    for iit = 1:Nx
        for jt = 1:Ny
                if J(jt,iit)
                                MARKED(jt,iit,1) = 1;
                                MARKED(jt,iit,2) = 1;
                                MARKED(jt,iit,3) = 1;
                                itt = itt + 1;
                                RRR(itt) = dat4MATH(jt,iit,1);
                                GGG(itt) = dat4MATH(jt,iit,2);
                                BBB(itt) = dat4MATH(jt,iit,3);
                end
        end
end
IM_r = mean(mean(dat4MATH(:,:,1)));
IM_g = mean(mean(dat4MATH(:,:,2)));
IM_b = mean(mean(dat4MATH(:,:,3)));
% subplot(3,3,11)
% imagesc(MARKED)
% axis equal image
% axis off
% colour = 'rgbrgb';
% sampname = 'RGB_MelVes';
% title( ' sampled' )
DataOut = [IM_r IM_g IM_b mean(RRR) mean(GGG) mean(BBB)];
%expression = sprintf(['save ' OutName ' DataOut x y MARKED dat4MATH J x y
%SeedFrac])
%
% cd Saved_Colors
% eval(expression);
% cd ..
%save RGB_MelVess DataOut x y MARKED dat4MATH
% figure(41)
% plot( [1 2 3 4 5 6], DataOut,'k*')
% %plot( [1 2 3 4 5 6], [IM_r IM_g IM_b mean(RRR) mean(GGG)
mean(BBB)],[colour])
% axis([ 0 7 0 max(DataOut)*1.2])
% xlabel('1-3 = RGBnormal 4-6 = RGBtarget')
% ylabel('Average Grayscale Value')
%expression = sprintf([ name_4Joel_temp(1:4) '_Levels']);
%cd Saved_Colors
%print(figure(41),'-djpeg','-r600', expression);
%cd ..
figure(7);clf
subplot(3,3,1)
imagesc(dat4MATH(:,:,1), [0 256]);
axis equal image
colormap gray
colorbar
axis off
```

TABLE 2-continued

```
title('R')
subplot(3,3,2)
imagesc(dat4MATH(:,:,2), [0 256]);
colormap gray
colorbar
axis equal image
axis off
title('G')
subplot(3,3,3)
imagesc(dat4MATH(:,:,3), [0 256]);
colormap gray
colorbar
axis equal image
axis off
title('B')
% aaa = dat4MATH(:,:,1) + dat4MATH(:,:,2) + dat4MATH(:,:,3);
% bbb = abs(log(dat4MATH(:,:1) + dat4MATH(:,:,2)));
% function1 = aaa .* bbb;
%
% subplot(3,3,6)
% imagesc(function1, [0 256]);
% colormap gray
% colorbar
% axis off
% title('F1          B/(R+G+B) * |log((R/G))|')
function2 = dat4MATH(:,:,1)./(dat4MATH(:,:,2) + dat4MATH(:,:,3));
%function3 = dat4MATH(:,:,1)./(dat4MATH(:,:,2) .* dat4MATH(:,:,3));
function3 = dat4MATH(:,:,1).^2./(dat4MATH(:,:,2) .* dat4MATH(:,:,3));
subplot(3,3,4)
imagesc(function2);
colormap gray
colorbar
axis equal image
axis off
title('F2          R/(G+B)')
subplot(3,3,5)
imagesc(function3);
hold on
plot(yt,xt,'rx')
colormap gray
colorbar
axis equal image
axis off
title('F3          R^2/(G*B)')
%functionRtoB
% figure(6);
% subplot(2,2,4)
% imagesc(QQQ)
% subplot(2,2,3)
% plot(Radial)
% hold on
% plot(i_catchRADPOW,val_catchRADPOW,'r*')
% xlabel(sprintf('Radius factor = %0.3f',factor_catch))
% ylabel('Frequency Power')
%function4 = abs(dat4MATH(:,:,1)−dat4MATH(:,:,2));
function4 = dat4MATH(:,:,1)−dat4MATH(:,:,2);
figure(7)
subplot(3,3,6)
imagesc(function4);
colormap gray
colorbar
axis equal image
axis off
title('F4          |R−G|')
function5 = function4 − function2.*function4;
normy = mean(mean(function5));
%figure(44);clf
subplot(3,3,7)
imagesc(function5)
colormap gray
axis equal image
axis off
colorbar
title('F5         [F4 − F2*F4]')
function5 = function5 − min(min(function5));
function5 = function5 − mean(mean(function5));
function5 = function5.*(function5>0);
function5 = function5 − 1;
function5 = function5.*(function5>0);
subplot(3,3,8)
```

TABLE 2-continued

```
imagesc(function5);
colormap gray
colorbar
axis equal image
axis off
title('F5 processed')
%figure(44)
clear BW
BW = function5>=max(max(function5))/FactorRED;
%subplot(2,2,1)
%imshow(BW)
%R=corrcoef(BW) ;
FindCorrDecay % factor_catch
maskVES = zeros(Ny,Nx);
figure(7)
colored = dat4MATH;
for i_ugh = 1:Nx
        %i_ugh
        for j_ugh = 1:Ny
                if functions(j_ugh, i_ugh) > max(max(functions))/FactorRED &
                mole(j_ugh,i_ugh)
                        % 210 --> 5
                        maskVES(j_ugh,i_ugh) = 1;
                        colored(j_ugh, i_ugh, 1) = max(max(max(dat4MATH)));
                        colored(j_ugh, i_ugh, 2) = 0;
                        colored(j_ugh, i_ugh, 3) =0;
        end
%               if function3(j_ugh, i_ugh) > max(max(function3))/2.5; % it's dark deep
%               melanin
%                                  colored(j_ugh, i_ugh, 1) = 0;
%                                  colored(j_ugh, i_ugh, 2) = 0;
%                                  colored(j_ugh, i_ugh, 3) = 0;
%               end
        end
end
Ves_Flag = -1;
if sum(sum(maskVES)) > 3 & factor_catch < 0.16
        Ves_Flag = 1;
else
        Ves_Flag = 0;
end
% colored BW,1) = 1;
% colored BW,2) = 0;
% colored BW,3) = 0;
% colored(function3 > max(max(function3))/2.5,1) = 0;
% colored(function3> max(max(function3))/2.5,2) = 0;
% colored(function3 > max(max(function3))/2.5,3) = 0;
function6 = function4 - (1-function2).*function4;
subplot(3,3,9)
imagesc(function6);
colormap gray
colorbar
axis equal image
axis off
title ('F6       [F4 - (1-F2)*F4]')
figure(6)
subplot(2,2,2)
imagesc(colored/max(max(max(colored))));
axis equal image
axis off
if Ves_Flag
        title('Vessles found')
end
if Ves_Flag == 0
        title('No vessles found')
end
%namm = sprintf('Colors_%3.0d',i_ref);
% cd Saved_Colors
% expression = sprintf([ name_4Joel_temp(1:4) '_ClrFndr']);
% print(figure(7),'-djpeg','-r600', expression);
% expression = sprintf([ name_4Joel_temp(1:4) '_Corr']);
% print(figure(44),'-djpeg','-r600', expression) ;
% cd ..
```

The use of a variable or constant symbol, like the letter "M", to refer to more than one variable or constant, does not mean all such variables or constants so designated are required to have the same value. The foregoing description of the preferred embodiments is for illustration and is not to be deemed as limiting the invention defined by the following claims. The primary application of the invention is to detect melanoma in humans and to distinguish cancerous from non-cancerous lesions. However, in principle, the apparatus and methods have broad application in the detection and display of other skin diseases. Moreover, using the clock sweep method of analyzing multispectral image data according to the invention lends itself to the development of improved metrics and more discriminating classifiers for the detection of melanoma, without departing from the scope of the invention. The foregoing descriptions of a clinical apparatus and cellular phone apparatus enable the person of ordinary skill to practice variants thereof without departing from the scope of the invention.

What is claimed is:

1. A method for obtaining an indication of a likelihood of the presence or absence of skin disease in a subject, comprising the steps of:
   obtaining image data from the subject's skin with a camera; and
   using a computer processor to (1) create a line segment extending out from a center of a lesion on the subject's skin, (2) rotate the line segment about the center at a plurality of angles θ, (3) sample the image data at a plurality of pixels along the radius R of the line segment at said angles to obtain pixel samples of brightness measurements in the (R, θ) plane, and (4) process said pixel samples to obtain metrics and/or classifiers indicating a likelihood of the presence or absence of skin disease in the subject, said process excluding border detection.

2. The method according to claim 1, further comprising the step of sequentially acquiring M images of multispectral image data with the camera while illuminating the subject's skin at corresponding M different wavelengths that range from 300 nm to 950 nm, wherein each pixel sample is a set of M brightness measurements at each wavelength and M>1.

3. The method according to claim 1, further comprising the step of illuminating the subject's skin with light having wavelengths in the range 300 to 400 nm.

4. The method according to claim 1, further comprising the step of illuminating the subject's skin with light having wavelengths in the range 400 to 500 nm.

5. The method according to claim 1, wherein the processor computes a variation in the brightness of the pixels on the rotating line segment.

6. The method according to claim 1, wherein the processor computes a range of the mean brightness among the pixels on the rotating line segment.

7. The method according to claim 1, wherein the processor computes a standard deviation of the mean brightness among the pixels on the rotating line segment.

8. The method according to claim 1, wherein the processor computes a standard deviation of the standard deviation of the brightness among the pixels on the rotating line segment.

9. The method according to claim 1, wherein the processor computes a slope with which pixel brightness increases at the lesion border going from inside the lesion to outside the lesion.

10. The method according to claim 1, wherein the pixel brightness is replaced with a mathematical function of multiple pixel brightness levels from images at different wavelengths.

11. The method according to claim 1, wherein the processor computes the radial distance between the lesion borders as defined on images of different wavelengths.

12. The method according to claim 1, wherein the processor computes the geometric center of the lesion at each wavelength and derives a metric from the coordinates of the lesion centers at the various wavelengths.

13. The method according to claim 1, wherein the processor computes the length of the lesion border squared to the total lesion area and derives a metric defining the roughness of the border.

14. The method according to claim 1, wherein the processor computes the ratio of the mismatched area to the total lesion area when the lesion is flipped about any axis bisecting the lesion and derives a metric defining the asymmetry of the lesion.

15. The method according to claim 1, wherein the processor computes a fractal dimension of the image to obtain a metric.

16. The method according to claim 1, further comprising the step of displaying at least one of: a blue color in the lesion; a black color in the lesion; one or more blood vessels within the lesion; and a negative network of pigment consisting of a branching light pattern within a darkly pigmented lesion identified by an image processing algorithm.

17. The method according to claim 2, wherein the spectral measurement is fit as the weighted sum of N chromophores.

18. The method according to claim 1, wherein the subject is human.

19. The method according to claim 1, wherein the skin disease is cancer.

20. The method according to claim 1, wherein the skin disease is melanoma.

21. A method for obtaining an indication of a likelihood of the presence or absence of skin disease in a subject, comprising the steps of:
   obtaining multispectral image data comprising M images sequentially acquired from the subject's skin with a camera while illuminating the subject's skin at corresponding M different wavelengths, whereby the wavelengths range from 300 nm to 950 nm and M>1; and
   using a computer processor to (1) create a line segment extending out from a center of a lesion on the subject's skin, (2) rotate the line segment about the center at a plurality of angles θ, (3) sample the image data at a plurality of pixels along the radius R of the line segment at said angles to obtain pixel samples in the (R, θ) plane each comprising a set of M brightness measurements corresponding to the respective M images, and (4) process said pixel samples to obtain metrics and/or classifiers indicating a likelihood of the presence or absence of skin disease in the subject.

22. A method according to claim 1, wherein the plurality of angles encompasses at least 360°.

23. A method according to claim 21, wherein the plurality of angles encompasses at least 360°.

24. A method according to claim 21, wherein said metrics and/or classifiers are based on processing the pixel samples at each different wavelength separately.

25. A method according to claim 21, wherein said metrics and/or classifiers are based on processing the pixel samples at each different wavelength together.

26. A method according to claim 25, wherein said metrics and/or classifiers are based on comparing the pixel samples at each different wavelength.

27. A method according to claim 25, wherein said metrics and/or classifiers are based on combining the pixel samples at each different wavelength.

28. A method for obtaining an indication of a likelihood of the presence or absence of skin disease in a subject, comprising the steps of:

obtaining multispectral image data comprising M images sequentially acquired from the subject's skin with a camera while illuminating the subject's skin with respective spectra $L_1, L_2, L_{i-1}, L_i, \ldots L_M$; and using a computer processor to (1) create a line segment extending out from a center of a lesion on the subject's skin, (2) rotate the line segment about the center at a plurality of angles θ, (3) sample the image data at a plurality of pixels along the radius R of the line segment at said angles to obtain pixel samples in the (R, θ) plane each comprising a set of M brightness measurements $\{I\_L_1, I\_L_2, I\_L_{i-1}, I\_L_i \ldots I\_L_M\}$ corresponding to the respective M images, (4) correct each pixel sample using brightness measurements at successive spectra, and (5) process said corrected pixel samples to obtain metrics and/or classifiers indicating a likelihood of the presence or absence of skin disease in the subject.

29. A method according to claim 28, wherein said correction at spectra $L_{i-1}$ is performed by subtracting $C*I\_L_i$ from $I\_L_{i-1}$, where C is a constant related to the amount of overlap between spectra $L_{i-1}$ and $L_i$.

* * * * *